US011731968B2

(12) United States Patent
Juchum et al.

(10) Patent No.: US 11,731,968 B2
(45) Date of Patent: Aug. 22, 2023

(54) TRICYCLIC PROTEIN KINASE INHIBITORS FOR PROMOTING LIVER REGENERATION OR REDUCING OR PREVENTING HEPATOCYTE DEATH

(71) Applicant: HEPAREGENIX GMBH, Tübingen (DE)

(72) Inventors: Michael Juchum, Heidelberg (DE); Roland Selig, Ulm (DE); Stefan Laufer, Tübingen (DE); Wolfgang Albrecht, Ulm (DE)

(73) Assignee: HepaRegeniX GmbH, Tübingen (DE)

( * ) Notice: Subject to any disclaimer, the term of this patent is extended or adjusted under 35 U.S.C. 154(b) by 266 days.

(21) Appl. No.: 17/254,071

(22) PCT Filed: Jun. 18, 2019

(86) PCT No.: PCT/EP2019/065995
§ 371 (c)(1),
(2) Date: Dec. 18, 2020

(87) PCT Pub. No.: WO2019/243315
PCT Pub. Date: Dec. 26, 2019

(65) Prior Publication Data
US 2021/0261545 A1  Aug. 26, 2021

(30) Foreign Application Priority Data
Jun. 21, 2018 (EP) .................. 18179035

(51) Int. Cl.
*C07D 471/04* (2006.01)
(52) U.S. Cl.
CPC ................ *C07D 471/04* (2013.01)
(58) Field of Classification Search
CPC ................................ C07D 471/04
See application file for complete search history.

(56) References Cited

U.S. PATENT DOCUMENTS

| 6,514,981 B1 | 2/2003 | Tang et al. |
| 11,040,027 B2 | 6/2021 | Albrecht et al. |
| 2020/0399241 A1 | 12/2020 | Scheidt et al. |
| 2021/0078995 A1 | 3/2021 | Praefke et al. |
| 2021/0261545 A1 | 8/2021 | Juchum et al. |
| 2022/0281864 A1 | 9/2022 | Albrecht et al. |
| 2022/0340561 A1 | 10/2022 | Pfaffenrot et al. |

FOREIGN PATENT DOCUMENTS

| CA | 3075477 A1 | 2/2019 | |
| CN | 112778311 A | 5/2021 | |
| CN | 113072497 A | 7/2021 | |
| EP | 2161271 A1 | 3/2010 | |
| EP | WO2010/025872 A2 * | 3/2010 | ........... C07D 471/04 |
| FR | 2876377 A1 | 4/2006 | |
| JP | 2006282745 A | 10/2006 | |
| RU | 2678455 C1 | 1/2019 | |
| WO | 2003035621 A1 | 5/2003 | |
| WO | 2003037898 A1 | 5/2003 | |
| WO | 2004058764 A1 | 7/2004 | |
| WO | 2007002325 A1 | 1/2007 | |
| WO | 2007002433 A1 | 1/2007 | |
| WO | 2007013896 A2 | 2/2007 | |
| WO | 2008063888 A2 | 5/2008 | |
| WO | 2008064255 A2 | 5/2008 | |
| WO | 2008064265 A2 | 5/2008 | |
| WO | 2008079903 A1 | 7/2008 | |
| WO | 2008079906 A1 | 7/2008 | |
| WO | 2010104945 A1 | 9/2010 | |
| WO | 2010111527 A1 | 9/2010 | |
| WO | 2010129567 A1 | 11/2010 | |
| WO | 2010129570 A1 | 11/2010 | |
| WO | 2011047432 A1 | 4/2011 | |
| WO | 2011079133 A2 | 6/2011 | |
| WO | 2012109075 A1 | 8/2012 | |
| WO | 2012129562 A2 | 9/2012 | |
| WO | 2012135631 A1 | 10/2012 | |
| WO | 2012136859 A1 | 10/2012 | |
| WO | 2013032951 A1 | 3/2013 | |
| WO | 2014035846 A2 | 3/2014 | |
| WO | 2014047648 A1 | 3/2014 | |
| WO | 2014194127 A1 | 12/2014 | |
| WO | 2017066193 A1 | 4/2017 | |
| WO | 2018134254 A1 | 7/2018 | |
| WO | 2019031990 A1 | 2/2019 | |
| WO | 2019149738 A1 | 8/2019 | |
| WO | 2020016243 A1 | 1/2020 | |
| WO | 2020051207 A2 | 3/2020 | |
| WO | 2020123675 A1 | 6/2020 | |

(Continued)

OTHER PUBLICATIONS

Torsten, W. et al. A Direct In Vivo RNAi Screen Identifies MKK4 as a Key Regulator of Liver Regeneration. Cell. 2013. 153:2 389-401 (Year: 2013).*
"Prevent." Merriam-Webster.com. 2022. https://www.merriam.webster.com/dictionary/prevent; Accessed Oct. 31, 2022.*
Asaoka, Y , "Diverse physiological functions of JNK signaling networks during early embryogenesis". Comparative Physiology and Biochemistry 30 (2), 59-67 (2013). [English Abstract].
ChemAbstract , Registry No. 1246614-25-4, 1 page (Oct. 20, 2010).
Deibler, K , et al., "A Chemical Probe Strategy for Interrogating Inhibitor Selectivity Across the MEK Kinase Family", ACS Chem Biol 12, 1245-1256, Supporting Information, 82 pages (2017).

(Continued)

Primary Examiner — Valerie Rodriguez-Garcia
Assistant Examiner — David M Shim
(74) Attorney, Agent, or Firm — Viksnins Harris Padys Malen LLP

(57) ABSTRACT

Tricyclic mitogen-activated protein kinases kinase 4 (MKK4) inhibitor compounds useful for promoting liver regeneration or reducing hepatocyte death by selectively inhibiting MKK4 over protein kinases JNK and MKK7.

11 Claims, No Drawings

(56) References Cited

FOREIGN PATENT DOCUMENTS

WO   2021018820 A1   2/2021
WO   2021144287 A1   7/2021

OTHER PUBLICATIONS

Deibler, K , et al., "Synthesis and Biological Evaluation of 3-Arylindazoles as Selective MEK4 Inhibitors", ChemMedChem 14, 615-620 (2019).
Erion, M , et al., "Liver-Targeted Drug Delivery Using HepDirect1 Prodrugs", Journal of Pharmacology and Experimental Therapeutics 312(2), 554-560 (2005).
Grueninger, F , et al., "Novel screening cascade identifies MKK4 as key kinase regulating Tau phosphorylation at Ser422", Mol Cell Biochem 357, 199-207 (2011).
Hu, G , et al., "MicroRNA-145 attenuates TNF-α-driven cartilage matrix degradation in osteoarthritis via direct suppression of MKK4", Cell Death and Disease 8, e3140, 13 pages (2017).
Kim, D , et al., "Novel Small Molecule Raf Kinase Inhibitors for Targeted Cancer Therapeutics", Arch Pharm Res 35(4), 605-612 (2012).
Krishna, S , et al., "A Fluorescence-Based Thermal Shift Assay Identifies Inhibitors of Mitogen Activated Protein Kinase Kinase 4", PLoS One 8(12), e81504, 11 pages (2013).
Ogura, M , et al., "Prenylated quinolinecarboxylic acid derivative prevents neuronal cell death through inhibition of MKK4", Biochemical Pharmacology 1-37, doi: https://doi.org/10.1016/j.bcp.2018.10.008 (2018).
Patent Cooperation Treaty, International Searching Authority, Search Report and Written Opinion for PCT/EP2019/065995, 9 pages, dated Sep. 18, 2019.
Schneider, C , et al., "Synthesis of 6-Substituted Pyrido[2,3-b]indoles by Electrophilic Substitution", Synlett 14, 2237-2241 (2007).
Vin, H , et al., "BRAF inhibitors suppress apoptosis through off-target inhibition of JNK signaling", eLife 2, e00969, DOI: 10.755/4/eLife.00969, 1-25 (2013).
Vin, H , et al., "BRAF inhibitors suppress apoptosis through off-target inhibition of JNK signaling", eLife 2, e00969, DOI: 10.7554/eLife.00969, 1-25, Supporting Information—Figures and Supplements (2013).
Wadsorth, A , et al., "A review of the synthesis of a-carbolines", European Journal of Medicinal Chemistry 97, 816-829 (2015).
Willenbring, H , et al., "A Therapy for Liver Failure Found in the JNK Yard", Cell 153, 283-284 (2013).
Wuestefeld, T , et al., "A Direct in Vivo RNAi Screen Identifies MKK4 as a Key Regulator of Liver Regeneration", Cell 153, 389-401 (2013).
U.S. Appl. No. 17/260,519.
U.S. Appl. No. 16/965,912, 2021-0078995.
U.S. Appl. No. 17/260,519, 2022-0281864.
U.S. Appl. No. 16/478,006, U.S. Pat. No. 11,040,027.
U.S. Appl. No. 17/630,105, 2022-0340561.
U.S. Appl. No. 17/792,685.
PUBCHEM , "Vemurafenib", CID No. 42611257, 54 pages (Create date: Jun. 22, 2009).

* cited by examiner

TRICYCLIC PROTEIN KINASE INHIBITORS FOR PROMOTING LIVER REGENERATION OR REDUCING OR PREVENTING HEPATOCYTE DEATH

The present invention relates to tricyclic protein kinase inhibitors which selectively inhibit mitogen-activated protein kinase kinase 4 (MKK4) over protein kinases JNK1 and MKK7.

BACKGROUND OF THE INVENTION

Liver diseases may be caused by infection, injury, exposure to toxic compounds, like alcohol or drugs, autoimmune processes, genetic defects, and other factors. Liver has a remarkable regenerative capacity which, however, may be impaired in disease state and may therefore be insufficient to compensate for the loss of hepatocytes and organ function. WO 2007/002433 describes compounds which are protein kinase inhibitors useful to treat diseases and conditions associated with aberrant activity of protein kinases. These compounds are inhibitors of Raf protein kinase, in particular B-Raf and c-Raf and mutations thereof and are therefore useful for cancer treatment. Further, they are said to inhibit a large variety of other protein kinases, among them c-Jun N-terminal kinases (JNK) and in particular JNK1. WO 2010/002325 and WO 2011/079133 have a similar disclosure and WO 2012/109075 and WO 2014/194127 disclose modified compounds having Raf protein kinase inhibiting activity. H. Vin et al. refer to two compounds of WO 2007/002433 as B-Raf inhibitors that suppress apoptosis through off-target inhibition of JNK signaling. WO 2010/111527 describes pyrazolo[3,4-b]pyridine compounds which are protein kinase inhibitors useful to treat a Raf protein kinase mediated disease or condition, like cancer. Further, they are said to inhibit a large variety of other protein kinases, among them c-Jun N-terminal kinases (JNK) and in particular JNK1. WO 2012/136859 discloses some compounds which are described as inhibitors of mitogen-activated protein kinase 4 (MKK4) and as being useful in the treatment of liver failure, for the protection of hepatocytes against apoptosis and for the regeneration of hepatocytes. Wuestefeld et al. (Cell 153:389-401, 2013) describe a functional genetic approach for the identification of gene targets that can be exploited to increase the regenerative capacity of hepatocytes. In particular, Wuestefeld et al. identify protein kinase kinase MKK4 as a key regulator of liver regeneration and report that MKK4 suppression increased hepatocyte regeneration via compensatory upregulation of MKK7 and a JNK1-dependent activation of ATF2 and ELK1. On the basis of the findings of the prior art it has been concluded that MKK4 and JNK1 inhibitors could be useful to treat JNK1-mediated diseases. However, it has been recognized in clinical treatments that treatment of liver diseases with such compounds failed.

SUMMARY OF THE INVENTION

The problem underlying the invention was to provide useful MKK4 inhibitors, in particular for treating liver diseases and especially for promoting liver regeneration or reducing or preventing hepatocyte death.

This problem was solved by providing the compounds of formula (I).

Thus, the invention comprises the following embodiments:
1. A compound having formula (I)

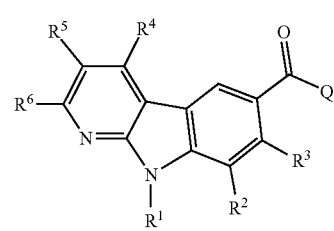

and the pharmaceutically acceptable salts, prodrugs, biologically active metabolites, solvates and stereoisomers thereof, wherein the variables in formula (I) have the meanings as follows:

$R^1$ is H or alkyl;
$R^2$ is H, alkyl or halogen;
$R^3$ is H, alkyl or halogen;
Q is phenyl, naphthyl or a heteroaromatic 5- or 6-membered monocyclic group wherein the heteroaromatic group has 1, 2 or 3 heteroatoms independently selected from O, N and S, and Q is substituted with $R^a$ and is optionally substituted with $R^b$, $R^c$, $R^d$ and $R^e$;
$R^a$ is $-NR^{10}SO_2R^{12}$, $-NR^{10}SO_2NR^{10}R^{12}$ or $-N=S(=O)R^{10}NR^{10}R^{10}$;
$R^b$, $R^c$, $R^d$ and $R^e$ are independently selected from
  a) H,
  b) alkyl which is optionally substituted with 1 or 2 substituents independently selected from phenyl, halogen substituted phenyl, halogen, OH, CN, and $-NR^{10}R^{10}$,
  c) halogen,
  d) hydroxyl,
  e) $-CN$,
  f) $-COOR^{10}$, and
  g) alkoxy,
wherein at least one of $R^b$, $R^c$, $R^d$ and $R^e$ is halogen;
$R^4$ is H, halogen, CN, or alkyl;
$R^5$ is selected from
  a) halogen;
  b) alkyl, which is optionally substituted with 1 or 2 groups independently selected from alkoxy, $-NR^{10}R^{10}$, $-COOR^{10}$, and oxadiazolyl;
  c) alkoxy;
  d) $C_3$-$C_6$-alkenyl, which is optionally substituted at the alkyl part thereof with 1, 2 or 3 groups independently selected from hydroxy, $-COOH$ or $-SO_2NH_2$;
  e) $C_3$-$C_6$-alkinyl, which is optionally substituted at the alkyl part thereof with 1, 2 or 3 groups independently selected from hydroxy, $-COOH$ or $-SO_2NH_2$;
  f) phenyl or naphthyl which phenyl or naphthyl is optionally substituted with 1, 2 or 3 groups independently selected from alkyl, halogen, haloalkyl, hydroxy, alkoxy, hydroxyalkyl, alkylthio, alkylsulfonyl, alkylsulfonyl-$NR^{10}$—, $R^{10}R^{10}N$—, $R^{11}O$—, benzyloxy, haloalkoxy, $-OCH_2O-$ (methylenedioxy attached in neighboring positions to the phenyl ring), $-OCH_2CH_2O-$ (ethylenedioxy attached in neighboring positions to the phenyl ring), $NO_2$, $-COOR^{10}$, $R^{10}OCO-$, $R^{10}R^{10}N-CO-$, $R^{10}R^{11}NSO_2-$, CN, alkylcarbonyl-$NR^{10}-$, alkenyl, carboxyl-substituted alkenyl, and a heteroaromatic 5- or 6-membered monocyclic or heteroaromatic 9- or 10-membered bicyclic group having 1, 2, 3 or 4 heteroatoms independently selected from O, N and S which group is optionally substituted with 1 or 2 groups independently selected from alkyl, alkoxy, halogen, —NR$^{10}$R$^{10}$, and alkyl which is optionally substituted with 1, 2 or 3 hydroxy groups, g) phenylalkenyl wherein the phenyl group is optionally substituted with 1, 2 or 3 groups independently selected from OH, alkoxy and —CONR$^{10}$R$^{10}$, h) a heteroaromatic 5- or 6-membered monocyclic or heteroaromatic 9- or 10-membered bicyclic group having 1 to 3 heteroatoms independently selected from O, N and S which group is optionally substituted with 1 or 2 groups independently selected from alkyl, alkoxy, —NR$^{10}$R$^{10}$, R$^{10}$R$^{11}$N—SO$_2$—, R$^{10}$R$^{11}$N—CO— and a heteroaromatic 5- or 6-membered group having 1, 2, 3 or 4 heteroatoms independently selected from O, N and S which group is optionally substituted with 1 or 2 groups independently selected from alkyl, alkoxy, halogen, —NR$^{10}$R$^{10}$, and alkyl which is optionally substituted with 1, 2 or 3 hydroxy groups;

R$^6$ is H, alkyl, alkoxy, or NR$^{10}$R$^{10}$;

R$^{10}$ at each occurrence independently is H, alkyl, phenyl, which is optionally substituted with 1 or 2 hydroxyl or alkoxy groups, or is phenylalkyl wherein the phenyl group is optionally substituted with halogen or alkyl;

R$^{11}$ is H, or alkyl, which is optionally substituted with 1 or 2 hydroxy groups;

R$^{12}$ is selected from a) alkyl, which is optionally substituted with 1 or 2 groups independently selected from alkyl, halogen, phenyl and cycloalkyl, b) heteroalkyl having 1, 2 or 3 heteroatoms independently selected from O, N and S, c) phenyl which is optionally substituted with 1 or 2 groups independently selected from alkyl, and halogen, and d) a heteroaromatic or non-aromatic heterocyclic 5- or 6-membered group having 1, 2 or 3 heteroatoms independently selected from O, N and S which group is optionally substituted with 1 or 2 groups independently selected from alkyl and halogen.

2. The compound of embodiment 1 having formula (Ia)

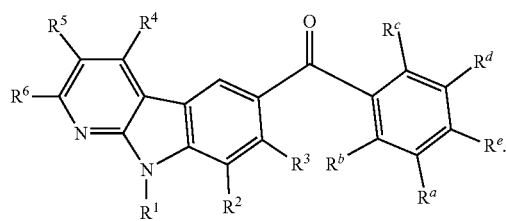

(Ia)

3. The compound of embodiment 1 or 2 having formula (Ib)

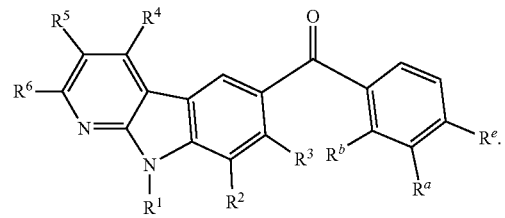

(Ib)

4. The compound of embodiment 1 or 2 having formula (Ic)

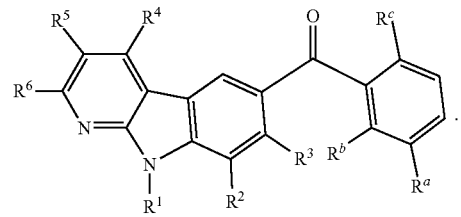

(Ic)

5. The compound of any one of embodiments 1 to 4, wherein R$^5$ is selected from a) halogen, b) alkoxy, c) C$_3$-C$_6$-alkenyl, which is optionally substituted at the alkyl part thereof with 1, 2 or 3 groups independently selected from hydroxy, —COOH or —SO$_2$NH$_2$, d) C$_3$-C$_6$-alkinyl, which is optionally substituted at the alkyl part thereof with 1, 2 or 3 groups independently selected from hydroxy, —COOH or —SO$_2$NH$_2$, e) phenyl or naphthyl which phenyl or naphthyl is optionally substituted with 1, 2 or 3 groups independently selected from alkyl, halogen, haloalkyl, hydroxy, alkoxy, hydroxyalkyl, alkylthio, alkylsulfonyl, alkylsulfonyl-NR$^{10}$—, R$^{10}$R$^{10}$N—, R$^{11}$O—, benzyloxy, haloalkoxy, —OCH$_2$O— (methylenedioxy attached in neighboring positions to the phenyl ring), —OCH$_2$CH$_2$O— (ethylenedioxy attached in neighboring positions to the phenyl ring), NO$_2$, COOR$^{10}$, R$^{10}$CO—, R$^{10}$R$^{10}$N—CO—, R$^{10}$R$^{11}$NSO$_2$—, CN, alkylcarbonyl-NR$^{10}$—, alkenyl, carboxyl-substituted alkenyl, and a heteroaromatic 5- or 6-membered monocyclic or heteroaromatic 9- or 10-membered bicyclic group having 1, 2, 3 or 4 heteroatoms independently selected from O, N and S which group is optionally substituted with 1 or 2 groups independently selected from alkyl, alkoxy, halogen, —NR$^{10}$R$^{10}$, and alkyl which alkyl is optionally substituted with 1, 2 or 3 hydroxy groups, and f) a heteroaromatic 5- or 6-membered monocyclic or heteroaromatic 9- or 10-membered bicyclic group having 1 to 3 heteroatoms independently selected from O, N and S which group is optionally substituted with 1 or 2 groups independently selected from alkyl, alkoxy, —NR$^{10}$R$^{10}$, R$^{10}$R$^{11}$N—SO$_2$—, R$^{10}$R$^{11}$N—CO— and a heteroaromatic 5- or 6-membered group having 1, 2, 3 or 4 heteroatoms independently selected from O, N and S which group is optionally substituted with 1 or 2 groups independently selected from alkyl, alkoxy, halogen, —NR$^{10}$R$^{10}$, and alkyl which is optionally substituted with 1, 2 or 3 hydroxy groups.

6. The compound of any one of embodiments 1 to 5, wherein $R^5$ is selected from
  a) halogen,
  b) alkoxy,
  c) phenyl or naphthyl which phenyl or naphthyl is optionally substituted with 1, 2 or 3 groups independently selected from alkyl, halogen, haloalkyl, hydroxy, alkoxy, hydroxyalkyl, alkylthio, alkylsulfonyl, alkylsulfonyl-$NR^{10}$—, $R^{10}R^{10}N$—, $R^{11}O$—, benzyloxy, haloalkoxy, —$OCH_2O$— (methylenedioxy attached in neighboring positions to the phenyl ring), —$OCH_2CH_2O$— (ethylenedioxy attached in neighboring positions to the phenyl ring), $NO_2$, $COOR^{10}$, $R^{10}CO$—, $R^{10}R^{10}N$—CO—, $R^{10}R^{11}NSO_2$—, CN, alkylcarbonyl-$NR^{10}$—, alkenyl, carboxyl-substituted alkenyl, and a heteroaromatic 5- or 6-membered monocyclic or heteroaromatic 9- or 10-membered bicyclic group having 1, 2, 3 or 4 heteroatoms independently selected from O, N and S which group is optionally substituted with 1 or 2 groups independently selected from alkyl, alkoxy, halogen, —$NR^{10}R^{10}$, and alkyl which alkyl is optionally substituted with 1, 2 or 3 hydroxy groups, and
  d) a heteroaromatic 5- or 6-membered monocyclic or heteroaromatic 9- or 10-membered bicyclic group having 1 to 3 heteroatoms independently selected from O, N and S which group is optionally substituted with 1 or 2 groups independently selected from alkyl, alkoxy, —$NR^{10}R^{10}$, $R^{10}R^{11}N$—$SO_2$—, $R^{10}R^{11}N$—CO— and a heteroaromatic 5- or 6-membered group having 1, 2, 3 or 4 heteroatoms independently selected from O, N and S which group is optionally substituted with 1 or 2 groups independently selected from alkyl, alkoxy, halogen, —$NR^{10}R^{10}$, and alkyl which is optionally substituted with 1, 2 or 3 hydroxy groups.

7. The compound of any one of embodiments 1 to 6, wherein $R^5$ is $C_3$-$C_4$-alkoxy, wherein the alkyl group is substituted with 1 or 2 hydroxy groups.

8. The compound of embodiment 7, wherein $R^5$ is halogen, in particular fluorine.

9. The compound of any one of embodiments 1 to 6, wherein $R^5$ is phenyl which is optionally substituted with 1, 2 or 3 groups independently selected from alkyl, halogen, haloalkyl, hydroxy, alkoxy, hydroxyalkyl, alkylsulfonyl, alkylsulfonyl-$NR^{10}$—, $R^{10}R^{10}N$—, $R^{11}O$—, $COOR^{10}$, $R^{10}R^{10}N$—CO—, $R^{10}R^{11}NSO_2$—, and a heteroaromatic 5- or 6-membered group having 1, 2, 3 or 4 heteroatoms independently selected from O, N and S which group is optionally substituted with 1 or 2 groups independently selected from alkyl, alkoxy, halogen, —$NR^{10}R^{10}$, and alkyl which alkyl is optionally substituted with 1, 2 or 3 hydroxy groups.

10. The compound of embodiment 9, wherein $R^5$ is phenyl which is optionally substituted with 1 or 2 groups independently selected from halogen, hydroxy, alkoxy, $R^{10}R^{10}N$—, $R^{11}$—, $COOR^{10}$, $R^{10}R^{10}N$—CO—, $R^{10}R^{11}NSO_2$—, tetrazolyl and triazolyl.

11. The compound of embodiment 10, wherein $R^5$ is phenyl which is substituted with 1 or 2 groups independently selected from halogen, hydroxy, $R^{10}R^{10}N$—, $R^{11}O$—, $COOR^{10}$, $R^{10}R^{10}N$—CO—, $R^{10}R^{11}NSO_2$—, and tetrazolyl.

12. The compound of any one of embodiments 1 to 6, wherein $R^5$ is a heteroaromatic 5- or 6-membered group having 1 to 3 heteroatoms independently selected from O, N and S which group is optionally substituted with 1 or 2 groups independently selected from alkyl, —$NR^{10}R^{10}$, $R^{10}R^{11}N$—$SO_2$—, $R^{10}R^{11}N$—CO— and a heteroaromatic 5- or 6-membered group having 1, 2, 3 or 4 heteroatoms independently selected from O, N and S which group is optionally substituted with 1 or 2 groups independently selected from alkyl or halogen.

13. The compound of any one of embodiments 1 to 6, wherein $R^5$ is a heteroaromatic 5- or 6-membered group having 1 to 3 heteroatoms independently selected from O, N and S which group is optionally substituted with 1 or 2 groups independently selected from —$NR^{10}R^{10}$, $R^{10}R^{11}N$—$SO_2$—, $R^{10}R^{11}N$—CO— and a heteroaromatic 5- or 6-membered group having 1 or 2 heteroatoms independently selected from O, N and S which group is optionally substituted with 1 or 2 alkyl groups.

14. The compound of embodiment 13, wherein $R^5$ is a heteroaromatic 5- or 6-membered group which comprises one nitrogen heteroatom and optionally an oxygen or sulfur heteroatom which group is optionally substituted with 1 or 2 groups independently selected from —$NR^{10}R^{10}$, $R^{10}R^{11}N$—$SO_2$—, $R^{10}R^{11}N$—CO— and a heteroaromatic 5- or 6-membered group having 1 or 2 heteroatoms independently selected from O, N and S which group is optionally substituted with 1 or 2 alkyl groups.

15. The compound of embodiment 13, wherein the heteroaromatic 5- or 6-membered group is pyridyl which group is optionally substituted with 1 or 2 groups independently selected from —$NR^{10}R^{10}$, $R^{10}R^{11}N$—$SO_2$—, $R^{10}R^{11}N$—CO— and pyrrolyl which is optionally substituted with 1 or 2 alkyl groups.

16. The compound of any one of the preceding embodiments, wherein Q is phenyl which is substituted as defined in embodiment 1.

17. The compound of any one of the preceding embodiments, wherein $R^a$ is —$NR^{10}SO_2R^{12}$.

18. The compound of any one of the preceding embodiments, wherein 1, 2 or 3 of $R^b$, $R^c$, $R^d$ and $R^e$ are halogen, in particular fluorine, and the other ones are H.

19. The compound of embodiment 18, wherein 1 of $R^b$, $R^c$, $R^d$ and $R^e$ is halogen, in particular fluorine, and the other ones are H.

20. The compound of embodiment 18, wherein 2 of $R^b$, $R^c$, $R^d$ and $R^e$ are halogen, in particular fluorine, and the other ones are H.

21. The compound of embodiment 18, wherein 3 of $R^b$, $R^c$, $R^d$ and $R^e$ are halogen, in particular fluorine, and the other ones are H.

22. The compound of any one of the preceding embodiments, wherein $R^1$, $R^2$, $R^3$, $R^4$, and $R^6$ are H or alkyl, in particular H.

23. The compound of any one of the preceding embodiments, wherein $R^{10}$ is H or alkyl, in particular H.

24. The compound of any one of the preceding embodiments, wherein $R^{11}$ is $C_2$-$C_4$-alkyl, which is substituted with 1 or 2 hydroxy groups.

25. The compound of any one of the preceding embodiments, wherein $R^{12}$ is alkyl, in particular $C_1$-$C_4$ alkyl, and most preferably methyl, ethyl, or propyl.

26. The compound of embodiment 5 having formula (Ib), wherein
$R^1$, $R^2$, $R^3$, $R^4$, and $R^6$ are H or alkyl, in particular H;
$R^5$ is selected from
  a) halogen,
  b) phenyl which is optionally substituted with 1 or 2 groups independently selected from halogen, hydroxy, $R^{10}R^{10}N$—, $R^{11}O$—, $COOR^{10}$, $R^{10}R^{10}N$—CO—, $R^{10}R^{11}NSO_2$—, and tetrazolyl, and c) pyridyl which is optionally substituted with 1 or 2 groups independently selected from —NR$^{10}$R$^{10}$, R$^{10}$R$^{11}$N—SO$_2$—, R$^{10}$R$^{11}$N—CO— and pyrrolyl which is optionally substituted with 1 or 2 groups independently selected from alkyl and halogen;

R$^a$ is —NR$^{10}$SO$_2$R$^{12}$;

R$^b$ and R$^e$ are halogen, in particular F;

R$^{10}$ is H or alkyl;

R$^{11}$ is H, or alkyl, which is optionally substituted with 1 or 2 hydroxy groups, and R$^{12}$ is alkyl.

27. The compound of embodiment 5 having formula (Ic), wherein

R$^1$, R$^2$, R$^3$, R$^4$, and R$^6$ are H or alkyl, in particular H;

R$^5$ is selected from
  a) halogen,
  b) phenyl which is optionally substituted with 1 or 2 groups independently selected from halogen, hydroxy, R$^{10}$R$^{10}$N—, R$^{11}$O—, COOR$^{10}$, R$^{10}$R$^{10}$N—CO—, R$^{10}$R$^{11}$NSO$_2$—, tetrazolyl and triazolyl, and
  c) pyridyl which is optionally substituted with 1 or 2 groups independently selected from —NR$^{10}$R$^{10}$, R$^{10}$R$^{11}$N—SO$_2$—, R$^{10}$R$^{11}$N—CO— and pyrrolyl which is optionally substituted with 1 or 2 groups independently selected from alkyl and halogen;

R$^a$ is —NR$^{10}$SO$_2$R$^{12}$;

R$^b$ and R$^c$ are halogen, in particular F;

R$^{10}$ is H or alkyl;

R$^{11}$ is H, or alkyl, which is optionally substituted with 1 or 2 hydroxy groups, and R$^{12}$ is alkyl.

DETAILED DESCRIPTION OF THE INVENTION

The compounds of formulae (I), (Ia), (Ib) and (Ic) and the pharmaceutically acceptable salts, solvates and optical isomers thereof, are MKK4 inhibitors and in particular MKK4 inhibitors which selectively inhibit protein kinase kinase MKK4 over protein kinases JNK1 and MKK7.

Further, the invention also relates to the compounds of formula (I), (Ia), (Ib) and (Ic) and the pharmaceutically acceptable salts, solvates and optical isomers thereof, for use in inhibiting protein kinase kinase MKK4 and in particular for use in selectively inhibiting protein kinase MKK4 over protein kinases JNK1 and MKK7.

Further, the invention also relates to said compounds for use in promoting liver regeneration or reducing or preventing hepatocyte death and, at the same time, increasing hepatocyte proliferation.

The invention also includes the pharmaceutically acceptable salts of the compounds mentioned above. The pharmaceutically acceptable salts are especially acid or base addition salts with pharmaceutically acceptable acids or bases. Examples of suitable pharmaceutically acceptable organic and inorganic acids are hydrochloric acid, hydrobromic acid, phosphoric acid, sulfuric acid, sulfamic acid, C$_1$-C$_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966. Examples of suitable pharmaceutically acceptable organic and inorganic bases are alkali metal hydroxides, such as sodium hydroxide or potassium hydroxide, alkaline earth metal hydroxides such as calcium or magnesium hydroxide, ammonium hydroxide, organic nitrogen bases such as dimethylamine, trimethylamine, ethanolamine, diethanolamine, triethanolamine, choline, 2-amino-2-hydroxymethyl-propane-1,3-diol, meglumine, procaine etc. L-arginine, L-lysine, ethylenediamine, or hydroxyethylpyrrolidine.

The invention also includes any tautomeric, crystal and polymorphic form of the compounds and salts of the present invention and mixtures thereof.

The invention also includes solvates such as hydrates.

The compounds of the invention may contain one or more chiral centers, and exist in different optically active forms such enantiomers and diastereomers.

As used herein, the term "pro-drug" refers to an agent which is converted into the parent drug in vivo by some physiological chemical process. An example, without limitation, of a pro-drug would be a compound of the present invention in the form of an ester.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue. Exemplary pro-drugs include, but are not limited to, compounds with carboxylic acid substituents wherein the free hydrogen is replaced by (C$_1$-C$_4$)alkyl, (C$_1$-C$_{12}$)alkanoyloxy-methyl, (C$_4$-C$_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyl-oxy)ethyl having from 4 to 7 carbon atoms, 1-methyl-1-(alkoxycarbonyloxy)-ethyl having from 5 to 8 carbon atoms, N-(alkoxycarbonyl) aminomethyl having from 3 to 9 carbon atoms, 1-(N-(alkoxycarbonyl)amino)ethyl having from 4 to 10 carbon atoms, 3-phthalidyl, 4-crotono-lactonyl, gamma-butyrolacton-4-yl, di-N,N—(C$_1$-C$_2$)alkylamino(C$_2$-C$_3$)alkyl (such as β-dimethylaminoethyl), carbamoyl-(C$_1$-C$_2$)alkyl, N,N-di (C$_1$-C$_2$)-alkylcarbamoyl-(C$_1$-C$_2$)alkyl and piperidino-, pyrrolidino- or morpholino(C$_2$-C$_3$)alkyl. Other exemplary pro-drugs release an alcohol wherein the free hydrogen of the hydroxyl substituent (e.g., R group contains hydroxyl) is replaced by (C$_1$-C$_6$)alkanoyloxy-methyl, 1-((C$_1$-C$_6$)alkanoyloxy)-ethyl, 1-methyl-1-((C$_1$-C$_6$)alkanoyloxy)ethyl, (C$_1$-C$_{12}$)alkoxy-carbonyloxy-methyl, N—(C$_1$-C$_6$)-alkoxy-carbonylaminomethyl, succinoyl, (C$_1$-C$_6$)alkanoyl, α-amino (C$_1$-C$_4$)alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, and salts thereof, —P(O)(O(C$_1$-C$_6$)alkyl)$_2$, phosponooxymethyl and salts and esters thereof, or glycosyl (the radical resulting from detachment of the hydroxyl of the hemiacetal of a carbohydrate). Particularly useful pro-drugs are liver targeting prodrugs such as phosphate and phosphonate prodrugs which are called HepDirect prodrugs (cf. Erion et al., The Journal of Pharmacology and Experimental Therapeutics, 312:554-560, 2005).

The expression MKK4 inhibitor means that the kinase activity of MKK4 is inhibited with an IC$_{50}$ of <10 μmol/l, preferably <1 μmol/l, and in particular <0.5 μmol/l. The expression "selectively inhibit protein kinase MKK4 over protein kinases JNK1 and MKK7" as used herein means that the ratio of MKK7 inhibiting activity to MKK4 inhibiting activity or the ratio of JNK1 inhibiting activity to MKK4 inhibiting activity, expressed as either percent of control or Kd, is ≥10, as measured with KINOMEscan™.

The expression "promoting liver regeneration or reducing or preventing hepatocyte death" as used herein means an increase in the relative number of proliferating hepatocytes by at least 30%, preferably at least 50%, as compared to the number of proliferating cells at the beginning of therapy. In particular, the expression means an increase by ≥100% when compared to the number of proliferating cells at the beginning of therapy. In this context, the experimental determination and quantification will be performed using standard methods, e.g. the quantification of the protein Ki67, which is strictly associated with cell proliferation. For quantification of proliferating hepatocytes in a tissue slide, several immunohistochemical standard methods are available, which use a primary anti-Ki67 antibody followed by visualization of anti-Ki67-binding by using, for example, a horseradish peroxidase conjugated secondary antibody. The amount of peroxidase activity, which is visualized by enzymatic conversion of chromogenic substrates, correlates with the amount of Ki67 protein and the number of proliferating cells.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine or chlorine.

Alkyl is a straight-chain or branched alkyl group which is preferably a $C_1$-$C_6$-alkyl group, i.e. an alkyl group having from 1 to 6 carbon atoms, and more preferably a $C_1$-$C_4$-alkyl group. Examples of an alkyl group are methyl, ethyl, n-propyl, iso-propyl, n-butyl, 2-butyl, iso-butyl, tert-butyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The definition of alkyl is likewise applicable to any group which includes an alkyl group.

Haloalkyl is a halogenated alkyl group as defined above, wherein at least one, e.g. 1, 2, 3, 4 or all of the hydrogen atoms are replaced by 1, 2, 3, 4 or a corresponding number of identical or different halogen atoms, such as trifluoromethyl, chloromethyl, bromomethyl, difluoromethyl, fluoromethyl, difluoroethyl, etc. Particular examples include the fluorinated $C_1$-$C_4$ alkyl groups as defined, such as trifluoromethyl, difluoromethyl, fluoromethyl, or difluoroethyl.

Cycloalkyl is a cycloaliphatic radical which is preferably $C_3$-$C_8$-cycloalkyl, i.e. a cycloalkyl group having from 3 to 8 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is >C=O.
Aminocarbonyl is $NH_2C(O)$—.
Alkenyl is a singly unsaturated hydrocarbon radical which is preferably a $C_2$-$C_6$-alkenyl group, i.e. an alkenyl group having 2, 3, 4, 5 or 6 carbon atoms, e.g. vinyl, allyl (2-propen-1-yl), 1-propen-1-yl, 2-propen-2-yl, methallyl(2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl, 2-hexen-1-yl.

Alkinyl is a singly unsaturated hydrocarbon radical which is preferably a $C_2$-$C_6$-alkinyl group, i.e. an alkinyl group having 2, 3, 4, 5 or 6 carbon atoms, e.g. ethynyl, 2-propyn-1-yl, 1-propyn-1-yl, 2-propyn-2-yl and the like. $C_3$-$C_5$-Alkinyl is, in particular, 2-propyn-1-yl, 2-butyn-1-yl, 3-butyn-1-yl, 2-pentyn-1-yl, 3-pentyn-1-yl, 4-pentyn-1-yl.

Alkylene is straight-chain or branched alkylene group which is preferably a $C_1$-$C_5$-alkylene group, i.e. an alkylene group having from 1 to 5 carbon atoms. Examples include methylene, ethylene and 1-methylethylene. A further example is propylene. Another further example is butylene. The definition of alkylene is likewise applicable to any group which includes an alkylene group.

Heteroalkylene is a straight-chain or branched alkyl group having 1, 2 or 3 heteroatoms which are selected from oxygen, nitrogen and sulfur. Examples for heteroalkylene are alkyloxyalkyl, alkylaminoalkyl, dialkylaminoalkyl or alkylthioalkyl. Any alkyl or alkylene group is as defined above. Alkyloxyalkyl is preferred.

Aryl (or aromatic group) is a 6- to 12-membered, in particular 6- to 10-membered, aromatic cyclic radical which can be a monocyclic aromatic ring, for example, phenyl etc., or a fused polycyclic aromatic ring comprising a first monocyclic aromatic ring and one or more carbocycles which are saturated, partially unsaturated or aromatic, for example, naphthyl, indenyl, tetrahydronaphthyl, indanyl.

A heteroaromatic (or heteroaryl) group is a 5- or 6-membered monocyclic or 9- or 10-membered bicyclic aromatic group having 1, 2 or 3 heteroatoms selected from O, N or S. The heteroaryl or heteroaromatic group may be bound to the neighboring group via a carbon atom (C-bound) or via a nitrogen heteroatom (N-bound). The heterocyclic radicals may be bound via a carbon atom (C-bound) or a nitrogen atom (N-bound). Preferred heteroaromatic radicals comprise 1 nitrogen atom as ring member atom and optionally 1 or 2 further heteroatoms as ring members, which are selected, independently of each other from O, S and N. Examples are:

C-bound, 5-membered, heteroaromatic rings:
2-furyl, 3-furyl, 5-furyl, 2-thienyl, 3-thienyl, 5-thienyl, pyrrol-2-yl, pyrrol-3-yl, pyrrol-5-yl, pyrazol-3-yl, pyrazol-4-yl, pyrazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol-5-yl, oxazol-2-yl, oxazol-4-yl, oxazol-5-yl, thiazol-2-yl, thiazol-4-yl, thiazol-5-yl, 1,2,3-oxadiazol-imidazol-4-yl, 4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings:
pyridin-2-yl, pyridin-3-yl (3-pyridyl), pyridin-4-yl (4-pyridyl), pyridin-5-yl, pyridazin-3-yl, pyridazin-4-yl, pyridazin-6-yl, pyrimidin-2-yl, pyrimidin-4-yl, pyrimidin-5-yl, pyrazin-2-yl, pyrazin-5-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings:
pyrrol-1-yl, pyrazol-1-yl, imidazol-1-yl, 1,2,3-triazol-1-yl, 1,2,4-triazol-1-yl.

Bicyclic heteroaromatic groups include one of the described 5- or 6-membered heteroaromatic rings and a further anellated, saturated or unsaturated or aromatic carbocycle, such as a benzene, cyclohexane, cyclohexene or cyclohexadiene ring. Examples are quinolinyl, isoquinolinyl, indolyl, indolizinyl, isoindolyl, 4-, 5-, 6- or 7-azaindole, indazolyl, benzofuryl, benzothienyl, benzo[b]thiazolyl, benzoxazolyl, benzthiazolyl, benzimidazolyl, imidazo[b]thiazolyl, thieno[b]pyridyl, imidazo[a]pyridyl, pyrazo[a]pyridyl and pyrrol[d]pyrimidyl. Examples of 5- or 6-membered heteroaromatic compounds comprising an anellated cycloalkenyl ring include dihydroindolyl, dihydroindolizinyl, dihydroisoindolyl, dihydroquinolinyl, dihydroisoquinolinyl, dihydrobenzofuryl, chromenyl, chromanyl, dihydropyrrol[a]imidazolyl and tetrahydrobenzothiazolyl.

A non-aromatic 5- or 6-membered group (heterocyclic group) may be saturated or partially unsaturated and includes 1, 2 or 3 heteroatoms selected from O, N and S. The heterocyclic radicals may be bound via a carbon atom (C-bound) or a nitrogen atom (N-bound). Preferred heterocyclic groups comprise 1 nitrogen atom as ring member atom and optionally 1 or 2 further heteroatoms as ring members, which are selected, independently of each other from O, S and N. Examples are:

C-bound, 5-membered, saturated rings, such as
tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 5-membered, saturated rings, such as
tetrahydropyrrol-1-yl (pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as
piperidin-1-yl, hexahydropyrimidin-1-yl, hexahydropyrazin-1-yl (piperazin-1-yl), hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholin-1-yl), tetrahydro-1,2-oxazin-2-yl;

C-bound, 5-membered, partially unsaturated rings, such as
2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl-, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydro-pyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetra-hydropyridazin-5-yl, 1,2,5,6-tetrahydropyridazin-6-yl, 1,2,3,6-tetrahydro-pyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Any group containing heteroatoms may contain 1, 2 or 3 heteroatoms which may be the same or different.

The compounds of the invention can be prepared starting out from 3-chloro-9H-pyrido[2,3-b]indole as an intermediate which can be obtained in analogy to the method disclosed in WO 2016/000827. The intermediate can be converted to the compounds of the invention in analogy to the methods as disclosed in WO 2007/002433 and WO 2007/002325. These WO-publications are incorporated herein in their entirety by reference. The acid or base addition salts are prepared in a customary manner by mixing the free base with a corresponding acid or by mixing the free acid with the desired base. Optionally, the reaction is carried out in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds of the invention are useful for promoting liver regeneration or reducing or preventing hepatocyte death and, at the same time, increasing hepatocyte proliferation. The compounds are therefore useful in treating, modulating, improving or preventing diseases which involve acute or chronic damages to the liver that may be caused by infection, injury, exposure to toxic compounds, an abnormal build-up of normal substances in the blood, an autoimmune process, a genetic defect or unknown causes.

Such liver diseases comprise all diseases where increased liver regeneration and reduction or prevention of hepatocyte death may be helpful to achieve a potential therapeutic effect, i.e. partial or complete restoration of liver functions. Such diseases comprise acute and chronic or acute on chronic liver diseases such as acute and chronic viral hepatitis like hepatitis B, C, E, hepatitis caused by Epstein-Barr virus, cytomegalovirus, herpes simplex virus and other viruses, all types of autoimmune hepatitis, primary sclerosing hepatitis, alcoholic hepatitis;

metabolic liver diseases such as metabolic syndrome, fatty liver like non-alcoholic fatty liver (NAFL), non-alcoholic steatohepatitis (NASH), alcoholic steatohepatitis (ASH), Morbus Wilson, Hemochromatosis, alpha1-antitrypsin deficiency, glycogen storage diseases;

all types of liver cirrhosis, such as primary biliary cirrhosis, ethyl toxic liver cirrhosis, cryptogenic cirrhosis;

acute (fulminant) or chronic liver failure such as toxic liver failure like acetaminophen (paracetamol) induced liver failure, alpha-amanitin induced liver failure, drug induced hepatotoxicity, liver failure caused, for example, by antibiotics, nonsteroidal anti-inflammatory drugs and anticonvulsants, acute liver failure induced by herbal supplements (kava, ephedra, skullcap, pennyroyal etc), liver disease and failure due to vascular diseases such as Budd-Chiari syndrome, acute liver failure of unknown origin, chronic liver disease due to right heart failure;

galactosemia, cystic fibrosis, porphyria, hepatic ischemia perfusion injury, small for size syndrome after liver transplantation, primary sclerosing cholangitis or hepatic encephalopathy.

For promoting liver regeneration or reducing or preventing hepatocyte death the compounds of the invention are administered to a patient in need thereof in a therapeutically effective amount. Various diagnostic methods are available to detect the presence of a liver disease. Blood levels of alanine aminotransferase (ALT) and aspartate aminotransferase (AST), above clinically accepted normal ranges, are known to be indicative of on-going liver damage. Blood bilirubin levels or other liver enzymes may be used as detection or diagnostic criteria. Routine monitoring of liver disease patients for blood levels of ALT and AST is used to measure progress of the liver disease while on medical treatment. Reduction of elevated ALT and AST levels to within the accepted normal range is taken as clinical evidence reflecting a reduction in the severity of the patients' liver damage. Commercial assays such as FibroTest/FibroSURE, HepaScore®, FibroMeter or Cirrhometer evaluate the combined results of five and more biochemical parameters for the detection of liver steatosis, fibrosis and cirrhosis. Furthermore, non-invasive, innovative physical imaging techniques such as magnetic resonance imaging, sonography and, in particular, elastography techniques are available to detect and monitor the status and progression of liver diseases.

It has further been found that shRNA mediated MKK4 suppression attenuate TNF-α-driven cartilage matrix degradation in osteoarthritis (Cell Death and Disease (2017) 8, e3140). Therefore, inhibition of the activity of MKK4 using the compounds of the invention are further useful for treating osteoarthritis and rheumatoid arthritis.

The compounds of the invention are customarily administered in the form of pharmaceutical compositions which comprise at least one compound according to the invention, optionally together with an inert carrier (e.g. a pharmaceutically acceptable excipient) and, where appropriate, other drugs. These compositions can, for example, be administered orally, rectally, transdermally, subcutaneously, intraperitoneally, intravenously, intramuscularly or intranasally.

Examples of suitable pharmaceutical compositions are solid medicinal forms, such as powders, granules, tablets, in particular film tablets, lozenges, sachets, cachets, sugar-coated tablets, capsules, such as hard gelatin capsules and soft gelatin capsules, or suppositories, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resins; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], $4^{th}$ edition, Aulendorf: ECV-Editio-Cantor-Verlag, 1996.

The compounds of the invention may also be suitable for combination with other therapeutic agents. The invention therefore further relates to a combination comprising a compound of the invention with one or more further therapeutic agents, in particular for use in promoting liver regeneration or reducing or preventing hepatocyte death. The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of the invention and at least one further therapeutic agent are within the scope of the current invention. In one embodiment of adjunctive therapeutic administration as described herein, a patient is typically stabilized on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

Suitable agents for use in combination with the compounds of the inventions include for example:

ACC inhibitors such as TOFA (5-(tetradecyloxy)-2-furoic acid), GS 0976, and ACC inhibitors as disclosed in WO 2016/112305, angiotensin II receptor antagonists, angiotensin converting enzyme (ACE) inhibitors, such as enalapril, caspase inhibitors, such as emricasan, cathepsin B inhibitors, such as a mixed cathepsin B/hepatitis C virus NS3 protease inhibitor, such as VBY-376, CCR2 chemokine antagonists, such as a mixed CCR2/CCR5 chemokine antagonist like cenicriviroc, CCR5 chemokine antagonists, chloride channel stimulators, such as cobiprostone, cholesterol solubilizers, diacylglycerol 0-acyltransferase 1 (DGAT1) inhibitors, such as LCQ908, dipeptidyl peptidase IV (DPPIV) inhibitors, such as linagliptin, farnesoid X receptor (FXR) agonists, such as INT-747 (obeticholic acid) or GS-9674 (PX-102, Cilofexor), Fibroblast growth factor 19 analogs, such as NGM-292, a non-tumorigenic analog of FGF19, Fibroblast growth factor 21 analogs, such as Pegbelfermin (BMS-986036), a polyethylene glycol-modified (PEGylated) recombinant human FGF21 analog, FXR/TGR5 dual agonists, such as INT-767, galectin-3 inhibitors, such as GR-MD-02, glucagon-like peptide 1 (GLP1) agonists, such as liraglutide or exenatide, glutathione precursors, hepatitis C virus NS3 protease inhibitors, such as a mixed cathepsin B/hepatitis C virus NS3 protease inhibitor like VBY-376, HMG CoA reductase inhibitors, such as a statin like atorvastatin, 11ß-hydroxysteroid dehydrogenase (11ß-HSD1) inhibitors, such as RO5093151, IL-1ß antagonists, IL-6 antagonists, such as a mixed IL-6/IL-1ß/TNFα ligand inhibitor like BLX-1002, IL-10 agonists, such as peg-ilodecakin, IL-17 antagonists, such as KD-025, ileal sodium bile acid cotransporter inhibitors, such as SHP-626, leptin analogs, such as metreleptin, 5-lipoxygenase inhibitors, such as a mixed 5-lipoxygenase/PDE3/PDE4/PLC inhibitor like tipelukast, LPL gene stimulators, such as alipogene tiparvovec, lysyl oxidase homolog 2 (LOXL2) inhibitors, such as an anti-LOXL2 antibody like GS-6624, PDE3 inhibitors, such as a mixed 5-lipoxygenase/PDE3/PDE4/PLC inhibitor like tipelukast, PDE4 inhibitors, such as ASP-9831 or a mixed 5-lipoxygenase/PDE3/PDE4/PLC inhibitor like tipelukast, phospholipase C (PLC) inhibitors, such as a mixed 5-lipoxygenase/PDE3/PDE4/PLC inhibitor like tipelukast, PPARα agonists, such as a mixed PPARα/δ agonist like GFT505 (elafibranor), PPARγ agonists, such as pioglitazone, PPARδ agonists, Rho associated protein kinase 2 (ROCK2) inhibitors, such as KD-025, sodium glucose transporter-2 (SGLT2) inhibitors, such as remogliflozin etabonate, stearoyl CoA desaturase-1 inhibitors, such as aramchol or CVT-12805, thyroid hormone receptor ß agonists, such as MGL-3196, tumor necrosis factor α (TNFα) ligand inhibitors, transglutaminase inhibitors and transglutaminase inhibitor precursors, such as mercaptamine, PTPIb inhibitors, such as A119505, A220435, A321842, CPT633, ISIS-404173, JTT-551, MX-7014, MX-7091, MX-7102, NNC-521246, OTX-001, OTX-002, or TTP814 and ASK1 inhibitors such as GS4977 (selonsertib).

In some embodiments, the one or more further therapeutic agents are selected from acetylsalicylic acid, alipogene tiparvovec, aramchol, atorvastatin, BLX-1002, cenicriviroc, cobiprostone, colesevelam, emricasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, GS-9674, remogliflozin etabonate, SHP-626, solithromycin, tipelukast, TRX-318, ursodeoxycholic acid, and VBY-376.

In some embodiments, one of the one or more further therapeutic agents is selected from acetylsalicylic acid, alipogene tiparvovec, aramchol, atorvastatin, BLX-1 002, and cenicriviroc.

In an embodiment the invention relates to a method of inhibiting protein kinase MKK4, selectively inhibiting protein kinase MKK4 over protein kinases JNK1 and MKK7, promoting liver regeneration or preventing hepatocyte death, treating acute, acute-on-chronic or chronic liver disease, treating acute and chronic or acute on chronic liver diseases such as acute and chronic viral hepatitis like hepatitis B, C, E, hepatitis caused by Epstein-Barr virus, cytomegalovirus, herpes simplex virus and other viruses, all types of autoimmune hepatitis, primary sclerosing hepatitis, alcoholic hepatitis;

treating metabolic liver diseases such as metabolic syndrome, fatty liver like non-alcoholic fatty liver (NAFL), non-alcoholic steatohepatitis (NASH), alcoholic steatohepatitis (ASH), Morbus Wilson, hemochromatosis, alpha1-antitrypsin deficiency, glycogen storage diseases;

treating all types of liver cirrhosis, such as primary biliary cirrhosis, ethyl toxic liver cirrhosis, cryptogenic cirrhosis;

treating acute (fulminant) or chronic liver failure such as toxic liver failure like acetaminophen (paracetamol) induced liver failure, alpha-amanitin induced liver failure, drug induced hepatotoxicity and liver failure caused, for example, by antibiotics, nonsteroidal anti-inflammatory drugs, anticonvulsants, acute liver failure induced by herbal supplements (kava, ephedra, skullcap, pennyroyal etc.), liver disease and failure due to vascular diseases such as Budd-Chiari syndrome, acute liver failure of unknown origin, chronic liver disease due to right heart failure;

treating galactosemia, cystic fibrosis, porphyria, hepatic ischemia perfusion injury, small for size syndrome after liver transplantation, primary sclerosing cholangitis or hepatic encephalopathy, or treating osteoarthritis or rheumatoid arthritis, which comprises administering an effective amount of a compound or a composition as defined above to a subject in need thereof.

In an embodiment, the compounds of the invention are administered in a dosage of 0.2 to 15 mg/kg or 0.5 to 12 mg/kg of the subject being treated. The compounds can be administered once or several times a day. The compounds are administered over 4 to 12 weeks in case of acute-on-chronic liver failure or alcoholic steatohepatitis and up to 52 weeks (and even longer) in cases of non-alcoholic fatty liver disease or non-alcoholic steatohepatitis.

The following examples illustrate the invention without limiting it.

EXAMPLES

Example 1: Synthesis of 3-chloro-9H-pyrido[2,3-b]indole

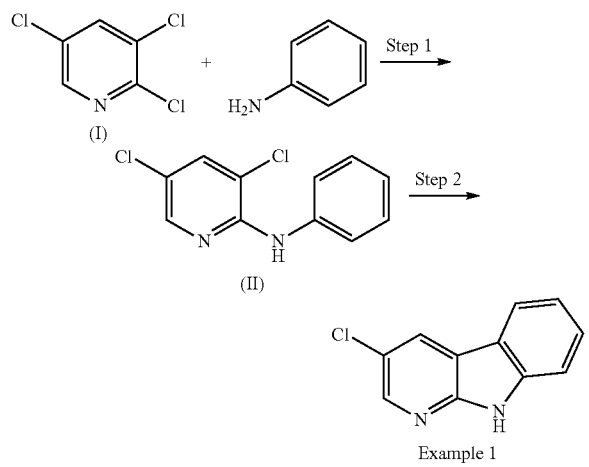

Example 1

Step 1: 3,5-dichloro-N-phenylpyridin-2-amine (II)

A mixture of 2,3,5-trichloropyridine (I), 2.50 g, 13.7 mmol), triphenylphosphine (0.719 g, 2.74 mmol), potassium t-butoxide (1.85 g, 16.4 mmol) and palladium(II) acetate (0.308 g, 1.37 mmol) was dissolved in dry o-xylene (25.0 mL) under argon and was treated with aniline (1.25 mL, 13.7 mmol) while stirring. The dark brown solution was stirred at 120° C. overnight. The suspension was filtered through a pad of Celite® and the filter was washed with ethyl acetate (20.0 mL). The filtrate was evaporated, the obtained residue was dissolved in ethyl acetate (20.0 mL) and washed twice with brine (10 mL). The organic layer was dried over sodium sulfate, filtered and the solvent was removed under vacuum. The residue was purified via flash chromatography (silica, gradient: 100% n-hexane→n-hexane/ethyl acetate 95/5 v/v. The product was obtained as yellow oil (1.449 g, 43%). $^1$H-NMR (200 MHz, CDCl$_3$) δ 8.09 (d, J=2.3 Hz, 1H), 7.66-7.53 (m, 3H), 7.43-7.30 (m, 2H), 7.15-7.02 (m, 1H), 6.96 (s, 1H). $^{13}$C-NMR (50 MHz, CDCl$_3$) δ 149.8, 144.3, 139.3, 136.4, 129.1, 123.3, 121.0, 120.1, 116.2. TLC-MS (ESI$^+$): Calculated 238.01 for C$_{11}$H$_8$Cl$_2$N$_2$. Measured 238.8 for [M+H]$^+$. HPLC: $t_R$=9.32 min, purity: 99.8% (254.4 nm), 96.6% (230.4 nm).

Step 2: 3-chloro-9H-pyrido[2,3-b]indole 3,5-dichloro-N-phenylpyridin-2-amine (II), 0.50 g, 2.05 mmol), tricyclohexylphosphine (0.115 g, 0.411 mmol), palladium(II) acetate (0.046 g, 0.205 mmol) and 1,8-diazabicyclo[5.4.0]un-dec-7-ene (0.614 mL, 4.11 mmol) were combined in a 1/1 v/v mixture of N,N-dimethyl-acetamide (0.250 mL) and o-xylene (0.250 mL) under argon and heated at 150° C. for 4 h. The mixture was cooled down to room temperature, diluted with ethyl acetate (10.0 mL) and saturated ammonia chloride solution (5.0 mL). The organic layer was separated and the water layer was extracted with ethyl acetate. The combined organic layers were dried over sodium sulfate, filtrated and the solvent was removed under vacuum. The residue was purified via flash-chromatography (silica, gradient: 100% n-hexane→n-hexane/ethyl acetate 3/2 v/v). The product was obtained as a yellow solid (0.322 g, 77%). $^1$H-NMR (200 MHz, DMSO-d$_6$) δ 11.99 (s, 1H), 8.68 (d, J=2.4 Hz, 1H), 8.42 (d, J=2.3 Hz, 1H), 8.20 (d, J=7.7 Hz, 1H), 7.68-7.35 (m, 2H), 7.31-7.19 (m, 1H). $^{13}$C-NMR (50 MHz, DMSO-d$_6$) δ 150.2, 144.0, 139.7, 128.0, 127.5, 121.8, 121.7, 119.8, 119.6, 116.4, 111.5. TLC-MS (ESI$^+$): Calculated 202.03 for C$_{11}$H$_7$ClN$_2$. Measured 202.9 for [M+H]$^+$. HPLC: $t_R$=8.63 min, purity: 99.2% (254.4 nm), 99.1% (230.4 nm).

Example 2: Synthesis of Benzoic Acid Derivatives

Example 2a: Synthesis of 2,6-difluoro-3-(methylsulfonamido)benzoic Acid

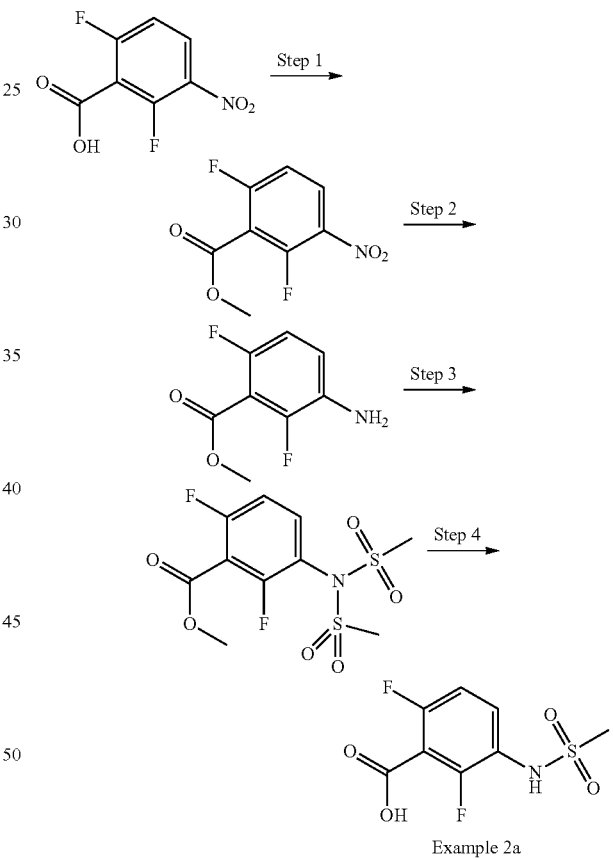

Example 2a

Step 1: methyl 2,6-difluoro-3-nitrobenzoate 2,6-Difluoro-3-nitrobenzoic acid (2.00 g, 9.85 mmol) was dissolved in dichloromethane (20.0 mL) under argon and was treated with N,N-dimethylformamide (0.050 mL) while stirring. Oxalyl chloride (0.93 mL, 10.8 mmol) was added dropwise and the solution was stirred at room temperature until gas evolution stopped. Methanol (0.44 mL, 10.8 mmol) was added dropwise and the reaction was stirred overnight. The reaction was quenched with aqueous saturated sodium hydrogencarbonate solution (5.0 mL). The organic layer was separated and the water layer was extracted with dichloromethane. The combined organic layers were dried over sodium sulfate, the solvent was removed under vacuum and the residue was purified via flash chromatography (silica, 100% n-hexane→n-hexane/ethyl acetate 7/3 v/v). The product was obtained as a white solid (1.23 g, 52%). $^1$H-NMR (200 MHz, CDCl$_3$) δ 8.23 (ddd, J=9.3, 8.2, 5.4 Hz, 1H), 7.12 (ddd, J=9.8, 8.0, 1.8 Hz, 1H), 4.00 (s, 3H). $^{13}$C NMR (50 MHz, CDCl$_3$) δ 163.1 (dd, J=266.9, 5.9 Hz), 160.1, 154.7 (dd, J=274.8, 7.4 Hz), 129.5 (dd, J=11.3, 1.3 Hz), 113.7 (dd, J=20.0, 18.3 Hz), 112.8 (dd, J=23.6, 4.6 Hz), 53.6. HPLC: $t_R$=5.46 min, purity: 98.5% (254.4 nm), 98.5% (230.4 nm).

Step 2: methyl 3-amino-2,6-difluorobenzoate

Methyl 2,6-difluoro-3-nitrobenzoate (1.13 g, 5.19 mmol) was dissolved in ethanol (17.0 mL) and palladium on activated charcoal (10% Pd) (0.055 g, 0.052 mmol) was added while stirring. The reaction was flushed with hydrogen until complete consumption of the starting material. The suspension was filtrated and the solvent of the filtrate was removed under vacuum. The residue was purified via flash chromatography (silica, gradient: 100% n-hexane→n-hexane/ethyl acetate 6/4 v/v). The product was obtained as yellow oil. $^1$H-NMR (200 MHz, DMSO-d$_6$) δ 7.00-6.82 (m, 2H), 5.26 (s, 2H), 3.86 (s, 3H). $^{13}$C-NMR (50 MHz, DMSO-d$_6$) δ 162.0, 149.8 (dd, J=240.7, 5.4 Hz), 146.6 (dd, J=247.6, 6.5 Hz), 133.7 (dd, J=12.9, 2.6 Hz), 118.2 (dd, J=8.9, 6.8 Hz), 111.6 (dd, J=22.0, 3.6 Hz), 110.1 (dd, J=20.0, 16.4 Hz), 52.8. TLC-MS (ESI$^-$): Calculated 187.04 for C$_8$H$_7$F$_2$NO$_2$. Measured 185.6 for [M−H]$^-$. HPLC: $t_R$=3.980 min, purity: 97.4% (254.4 nm), 97.6% (230.4 nm).

Step 3: methyl 3-[bis(methylsulfonyl)amino]-2,6-difluorobenzoate

Methyl 3-amino-2,6-difluorobenzoate (0.428 g, 2.29 mmol) was dissolved in dry dichloromethane (7.00 mL) under argon and triethylamine (0.96 mL, 6.86 mmol) was added. The stirring solution was cooled to 0° C. (ice bath) and methanesulfonyl chloride (0.39 mL, 5.03 mmol) was added dropwise. After stirring at 0° C. for 5 min, the ice bath was removed and the cloudy suspension was stirred at room temperature for 1 h. The reaction was quenched with ethyl acetate (20.0 mL) and water (5.0 mL), the organic layer was separated and the water layer was extracted with ethyl acetate. The combined organic layers were dried over sodium sulfate, filtrated and purified via flash chromatography (silica, gradient: 100% n-hexane→n-hexane/ethyl acetate 6/4 v/v). The product was obtained as an off-white solid (0.722 g, 91%). $^1$H-NMR (200 MHz, DMSO-d$_6$) δ 8.01 (td, J=8.7, 5.7 Hz, 1H), 7.44 (td, J=9.3, 1.8 Hz, 1H), 3.92 (s, 3H), 3.56 (s, 6H). TLC-MS (ESI$^+$): Calculated 343.00 for C$_{10}$H$_{11}$F$_2$NO$_6$S$_2$. Measured 365.8 for [M+Na]$^+$. HPLC: $t_R$=4.52 min, purity: 100.0% (254.4 nm), 98.5% (230.4 nm).

Step 4: 2,6-difluoro-3-(methanesulfonamido)benzoic Acid 2a

A solution of methyl 3-[bis(methylsulfonyl)amino]-2,6-difluorobenzoate (0.700 g, 2.02 mmol) in tetrahydrofurane (8.00 mL) and methyl alcohol (2.00 mL) was treated with 1 M sodium hydroxide solution (7.00 mL, 6.07 mmol) and was stirred at room temperature until HPLC revealed complete consumption of the starting material (4 h). Most of the solvent was removed under vacuum and the residue was adjusted to pH 4 with a 1M aqueous HCl solution. The solvent was removed under vacuum and the residual solid was purified via flash chromatography (silica, gradient: DCM (dichloromethane)/MeOH (methanol) 8/2 v/v→DCM/MeOH 6/4 v/v). The product was obtained as an off-white solid (0.447 g, 87%). $^1$H-NMR (200 MHz, DMSO-d$_6$) δ 9.46 (s, 1H), 7.16 (td, J=8.8, 6.0 Hz, 1H), 6.92 (td, J=8.9, 1.4 Hz, 1H), 2.97 (s, 3H). $^{13}$C NMR (50 MHz, DMSO) δ 162.3, 156.0 (dd, J=242.7, 10.0 Hz), 152.5 (dd, J=246.3, 11.4 Hz), 125.0 (d, J=8.8 Hz), 123.2-121.5 (m), 120.8 (dd, J=14.9, 3.6 Hz), 111.0 (dd, J=24.1, 3.8 Hz), 48.6. TLC-MS (ESI$^-$): Calculated 251.01 for C$_8$H$_7$F$_2$NO$_4$S. Measured 249.8 for [M−H]$^-$. HPLC: $t_R$=1.63 min, purity: 97.6% (254.4 nm), 99.6% (230.4 nm).

In analogy to this procedure, Examples 2b and 2c were prepared.

| Example | Chemical structure | Analytical data |
|---|---|---|
| 2a | (structure of 2,6-difluoro-3-(methanesulfonamido)benzoic acid) | $^1$H-NMR (200 MHz, DMSO-d$_6$) δ 9.46 (s, 1H), 7.16 (td, J = 8.8, 6.0 Hz, 1H), 6.92 (td, J = 8.9, 1.4 Hz, 1H), 2.97 (s, 3H). $^{13}$C NMR (50 MHz, DMSO-d$_6$) δ 162.3, 156.0 (dd, J = 242.7, 10.0 Hz), 152.5 (dd, J = 246.3, 11.4 Hz), 125.0 (d, J = 8.8 Hz), 123.2-121.5 (m), 120.8 (dd, J = 14.9, 3.6 Hz), 111.0 (dd, J = 24.1, 3.8 Hz), 48.6. TLC-MS (ESI$^-$): m/z 249.8 ([M − H]$^-$). HPLC: $t_R$ = 1.63 min, purity: 97.6% (254.4 nm), 99.6% (230.4 nm). |
| 2b | (structure of 2,6-difluoro-3-(ethanesulfonamido)benzoic acid) | $^1$H NMR (200 MHz, DMSO-d$_6$) δ 9.58 (s, 1H), 7.37-7.21 (m, 1H), 7.01 (t, J = 8.4 Hz, 1H), 3.05 (q, J = 7.3 Hz, 2H), 1.25 (t, J = 7.3 Hz, 3H). TLC-MS (ESI$^-$): Calculated 265.02 for C$_9$H$_9$F$_2$NO$_4$S. Measured 264.0 for [M − H]$^-$. HPLC: $t_R$ = 1.68 min, purity: 98.3% (254.4 nm), 99.3% (230.4 nm). |

| Example | Chemical structure | Analytical data |
|---|---|---|
| 2c | (structure shown) | $^1$H NMR (200 MHz, DMSO-$d_6$): δ 14.01 (s, 1H), 9.74 (s, 1H), 7.54 (dd, J = 14.8, 8.7 Hz, 1H), 7.20 (t, J = 9.2 Hz, 1H), 3.15-3.02 (m, 2H), 1.85-1.63 (m, 2H), 0.97 (t, J = 7.4 Hz, 3H). $^{13}$C NMR (50 MHz, DMSO): δ 161.8, 157.3 (dd, J = 174.8, 6.9 Hz), 152.3 (dd, J = 178.1, 6.9 Hz), 129.8 (dd, J = 10.2, 2.2 Hz), 122.0 (dd, J = 13.5, 3.8 Hz), 112.8 (dd, J = 21.3, 19.3 Hz), 112.3 (dd, J = 22.6, 4.1 Hz), 53.8, 16.9, 12.6. TLC-MS (ESI$^-$): Calculated 279.04 for $C_{10}H_{11}F_2NO_4S$. Measured 278.0 for [M − H]$^-$. |

Example 3: Synthesis of N-(3-(3-chloro-9H-pyrido[2,3-b]indole-6-carbonyl)-2,4-difluorophenyl)alkyl-1-sulfonamide Examples 3a, 3b and 3c were prepared by means of coupling the benzoic acid derivatives described in Example 2 with the product of Example 1 in a Friedel-Crafts acylation according to the following reaction scheme:

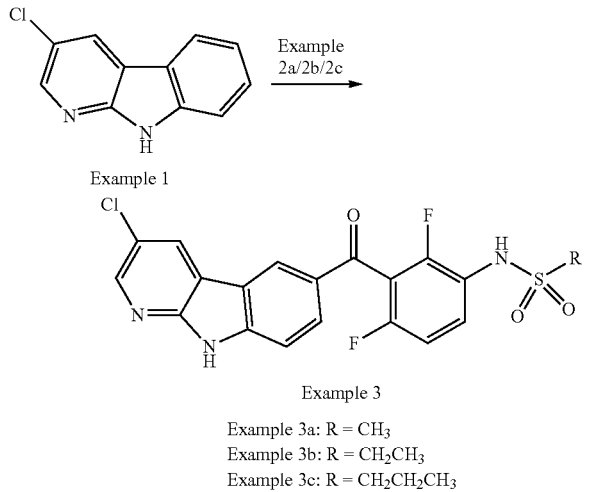

Example 3a: R = CH$_3$
Example 3b: R = CH$_2$CH$_3$
Example 3c: R = CH$_2$CH$_2$CH$_3$ The Experimental Procedure for Example 3c is Described in Detail:

2,6-difluoro-3-(propylsulfonamido)benzoic acid (0.493 mmol) was suspended in dry dichloromethane (2.50 mL) under argon and one drop of N,N-dimethylformamide was added while stirring. Oxalyl chloride (0.051 mL, 0.592 mmol) was added dropwise at room temperature and the reaction was further stirred at room temperature for 1 h. The clear brownish solution was added dropwise to a stirring suspension of 3-chloro-9H-pyrido[2,3-b]indole, 0.100 g, 0.493 mmol) and aluminium chloride (0.329 g, 2.47 mmol) in dichloromethane (4.0 mL) under argon. The brown suspension was stirred at room temperature for 4 h. The suspension was cooled (ice-bath) and quenched with MeOH (methanol) (10.0 mL). The resulting white suspension was evaporated to dryness. The residue was treated with ethyl acetate (30.0 mL) and saturated aqueous ammonium chloride solution (10.0 mL). After separating the organic layer, the water layer was extracted with ethyl acetate. The combined organic layers were dried over sodium sulfate and the solvent was removed under vacuum. The residue was purified via flash chromatography. Details are given in table 1 below:

TABLE 1

| Reactand 1 | Reactand 2 | Product | Analytical data |
|---|---|---|---|
| Example 1 | Example 2a | Example 3a | $^1$H-NMR (200 MHz, DMSO-$d_6$) δ 12.62 (s, 1H), 9.81 (s, 1H), 8.91 (d, J = 2.4 Hz, 1H), 8.81 (s, 1H), 8.51 (d, J = 2.3 Hz, 1H), 8.04 (dd, J = 8.6, 1.6 Hz, 1H), 7.75-7.58 (m, 2H), 7.35 (td, J = 9.0, 1.5 Hz, 1H), 3.09 (s, 3H). TLC-MS (ESI$^-$): Calculated 435.03 for $C_{19}H_{12}ClF_2N_3O_3S$. Measured 433.9 for [M–H]$^-$. |
| | Example 2b | Example 3b | $^1$H NMR (200 MHz, DMSO-$d_6$) δ 12.62 (s, 1H), 9.82 (s, 1H), 8.91 (d, J = 2.1 Hz, 1H), 8.80 (s, 1H), 8.50 (d, J = 2.3 Hz, 1H), 8.04 (d, J = 8.8 Hz, 1H), 7.76-7.57 (m, 2H), 7.34 (t, J = 8.8 Hz, 1H), 3.18 (q, J = 7.3 Hz, 2H), 1.26 (t, J = 7.3 Hz, 3H). TLC-MS (ESI$^-$): Calculated 449.04 for $C_{20}H_{14}ClF_2N_3O_3S$. Measured 448.0 for [M–H]$^-$. |
| | Example 2c | Example 3c | $^1$H-NMR (200 MHz, DMSO-$d_6$) δ 12.63 (s, 1H), 9.84 (s, 1H), 8.92 (d, J = 2.4 Hz, 1H), 8.81 (s, 1H), 8.50 (d, J = 2.4 Hz, 1H), 8.05 (dd, J = 8.7, 1.7 Hz, 1H), 7.76-7.58 (m, 2H), 7.34 (td, J = 8.9, 1.5 Hz, 1H), 3.24-3.10 (m, 2H), 1.85-1.62 (m, 2H), 0.94 (t, J = 7.4 Hz, 3H). $^{13}$C-NMR (50 MHz, DMSO-$d_6$) δ 187.0, 156.1 (dd, J = 246.8, 7.1 Hz), 152.2 (dd, J = 249.7, 8.6 Hz), 151.0, 145.3, 143.7, 129.4, |

| Reactand 1 | Reactand 2 | Product | Analytical data |
|---|---|---|---|
| | | | 129.2 (d, J = 9.5 Hz), 128.5, 128.2, 125.8, 123.0, 122.1 (dd, J = 13.5, 3.6 Hz), 119.8, 117.4 (dd, J = 23.4, 21.2 Hz), 116.7, 112.7 (d, J = 3.7 Hz), 112.2, 53.4, 16.8, 12.5. TLC-MS (ESI⁻): Calculated 463.06 for $C_{21}H_{16}ClF_2N_3O_3S$. Measured 461.9 for [M−H]⁻. |

Example 4: Synthesis of 3-substituted N-(2,4-difluoro-3-(9H-pyrido[2,3-b] indole-6-carbonyl)phenyl)propane-1-sulfonamides (4a-4n)

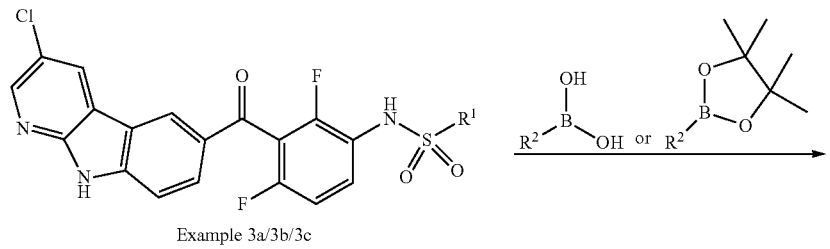

Example 3a/3b/3c

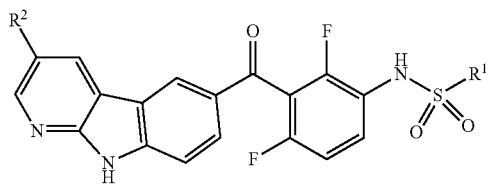

Examples 4a-4n

A mixture of 1 eq. of example 3a, 3b or 3c, boronic acid/boronic acid pinacol ester (1.3 eq.) and XPhos PdG₃/PdG₄ (commercially available) (0.05 eq.) was flushed with argon in a microwave tube for 12 min. A 4/1 v/v mixture of 1,4-dioxane and 1.5 M aqueous potassium carbonate solution (argon flushed) was added, the reaction was heated in a microwave (50 W, 110° C.) for 45 min. The reaction was quenched with ethyl acetate (15.0 mL) and saturated aqueous ammonium chloride solution (5.0 mL). The organic layer was separated, and the water layer was extracted with ethyl acetate. The combined organic layers were dried over sodium sulfate, filtered and the solvent was removed under vacuum. The residue was purified via flash chromatography (silica). Details are given in table 2 below:

TABLE 2

| Expl. | Reactand | Boronic acid/ Pinacol ester | Product | ¹H-NMR/MS |
|---|---|---|---|---|
| 4a | 3c | (4-pyridyl boronic acid) | (product structure) | ¹H-NMR (200 MHz, DMSO-d₆) δ 12.68 (s, 1H), 9.87 (s, 1H), 9.24 (s, 1H), 8.99 (s, 1H), 8.85 (s, 1H), 8.67 (d, J = 4.0 Hz, 2H), 8.05 (d, J = 9.0 Hz, 1H), 7.88 (d, J = 4.5 Hz, 2H), 7.79-7.53 (m, 2H), 7.36 (t, J = 8.6 Hz, 1H), 3.28-3.03 (m, 2H), 1.96-1.34 (m, 2H), 0.92 (t, J = 7.3 Hz, 3H). TLC-MS (ESI⁻): 504.8 ([M − H]⁻) |

TABLE 2-continued

| Expl. | Reactand | Boronic acid/ Pinacol ester | Product | ¹H-NMR/MS |
|---|---|---|---|---|
| 4b | 3c | (4-sulfamoylphenyl)boronic acid | sulfamoyl-phenyl β-carboline difluoro propylsulfonamide | ¹H-NMR (400 MHz, DMSO-d₆) δ 12.61 (s, 1H), 9.84 (s, 1H), 9.16 (d, J = 1.9 Hz, 1H), 8.91 (s, 1H), 8.84 (s, 1H), 8.08-7.99 (m, 3H), 7.95 (d, J = 8.3 Hz, 2H), 7.73-7.63 (m, 2H), 7.44 (s, 2H), 7.36 (t, J = 8.7 Hz, 1H), 1.80-1.68 (m, 2H), 0.92 (t, J = 7.4 Hz, 3H). TLC-MS (ESI⁻): 582.7 ([M − H]⁻) |
| 4c | 3c | (2-fluorophenyl)boronic acid | 2-fluorophenyl β-carboline difluoro propylsulfonamide | ¹H-NMR (400 MHz, DMSO-d₆) δ 12.59 (s, 1H), 9.83 (s, 1H), 8.93 (s, 1H), 8.83 (s, 1H), 8.67 (t, J = 1.9 Hz, 1H), 8.05 (dd, J = 8.6, 1.5 Hz, 1H), 7.72-7.60 (m, 3H), 7.50-7.43 (m, 1H), 7.40-7.30 (m, 3H), 3.20-2.94 (m, 2H), 1.80-1.59 (m, 2H), 0.90 (t, J = 7.4 Hz, 3H). TLC-MS (ESI⁻): 521.8 ([M − H]⁻) |
| 4d | 3c | (4-hydroxyphenyl)boronic acid | 4-hydroxyphenyl β-carboline difluoro propylsulfonamide | ¹H-NMR (400 MHz, DMSO-d6) δ 12.44 (s, 1H), 9.83 (s, 1H), 9.59 (s, 1H), 8.93 (d, J = 2.0 Hz, 1H), 8.80 (s, 1H), 8.73 (d, J = 2.1 Hz, 1H), 8.02 (d, J = 8.6 Hz, 1H), 7.72-7.56 (m, 4H), 7.35 (t, J = 8.7 Hz, 1H), 6.90 (d, J = 8.5 Hz, 2H), 3.22-3.08 (m, 2H), 1.80-1.67 (m, 2H), 0.92 (t, J = 7.4 Hz, 3H). TLC-MS (ESI⁻): 519.8 ([M − H]⁻) |
| 4e | 3c | (4-carbamoylphenyl)boronic acid | 4-carbamoylphenyl β-carboline difluoro propylsulfonamide | ¹H-NMR (200 MHz, DMSO-d₆) δ 12.58 (s, 1H), 9.85 (s, 1H), 9.15 (d, J = 2.0 Hz, 1H), 9.00-8.71 (m, 2H), 8.19-7.84 (m, 6H), 7.74-7.55 (m, 2H), 7.53-7.19 (m, 2H), 3.28-2.97 (m, 2H), 2.01-1.48 (m, 2H), 0.92 (t, J = 7.4 Hz, 3H). TLC-MS (ESI⁻): 547.0 ([M − H]⁻) |
| 4f | 3c | [4-(1H-tetrazol-5-yl)phenyl]boronic acid | tetrazolyl-phenyl β-carboline difluoro propylsulfonamide | ¹H-NMR (200 MHz, DMSO-d₆) δ 12.67 (s, 1H), 9.17 (s, 1H), 8.89 (d, J = 16.5 Hz, 2H), 8.23 (d, J = 8.3 Hz, 2H), 8.03 (t, J = 7.4 Hz, 3H), 7.80-7.56 (m, 2H), 7.36 (t, J = 7.8 Hz, 1H), 3.28-2.99 (m, 2H), 1.85-1.62 (m, 2H), 0.92 (t, J = 7.2 Hz, 3H). TLC-MS (ESI⁻): 571.7 ([M − H]⁻) |

TABLE 2-continued

| Expl. | Reactand | Boronic acid/ Pinacol ester | Product | ¹H-NMR/MS |
|---|---|---|---|---|
| 4g | 3c | | | TLC-MS (ESI⁻): 598.0 ([M − H]⁻) |
| 4h | 3c | | | ¹H NMR (200 MHz, DMSO-d₆) δ 12.57 (s, 1H), 9.84 (s, 1H), 9.16 (d, J = 1.3 Hz, 1H), 8.97-8.80 (m, 2H), 8.50 (t, J = 4.9 Hz, 1H), 8.12-7.88 (m, 5H), 7.77-7.60 (m, 2H), 7.36 (t, J = 8.8 Hz, 1H), 4.86 (d, J = 4.8 Hz, 1H), 4.61 (t, J = 5.7 Hz, 1H), 3.80-3.59 (m, 1H), 3.54-3.22 (m, 4H), 3.22-3.08 (m, 2H), 1.85-1.63 (m, 2H), 0.92 (t, J = 7.5 Hz, 3H). TLC-MS (ESI⁻): 620.7 for ([M − H]⁻) |
| 4i | 3c | | | ¹H NMR (200 MHz, DMSO-d₆) δ 12.61 (s, 1H), 9.85 (s, 1H), 9.16 (d, J = 1.7 Hz, 1H), 8.92 (d, J = 1.9 Hz, 1H), 8.84 (s, 1H), 8.05 (d, J = 8.2 Hz, 3H), 7.92 (d, J = 8.1 Hz, 2H), 7.77-7.52 (m, 3H), 7.35 (t, J = 8.6 Hz, 1H), 4.80 (d, J = 5.1 Hz, 1H), 4.56 (t, J = 5.3 Hz, 1H), 3.60-3.42 (m, 1H), 3.40-3.24 (m, 2H), 3.23-3.08 (m, 2H), 3.02-2.85 (m, 1H), 2.75-2.57 (m, 1H), 1.87-1.61 (m, 2H), 0.92 (t, J = 7.4 Hz, 3H). TLC-MS (ESI⁻): 656.8 ([M − H]⁻) |
| 4j | 3a | | | ¹H-NMR (400 MHz, DMSO-d₆) δ 12.61 (s, 1H), 9.82 (s, 1H), 9.15 (d, J = 2.1 Hz, 1H), 8.91 (d, J = 2.2 Hz, 1H), 8.85 (s, 1H), 8.04 (d, J = 8.5 Hz, 3H), 7.95 (d, J = 8.5 Hz, 2H), 7.73-7.63 (m, 2H), 7.44 (s, 2H), 7.36 (t, J = 8.7 Hz, 1H), 3.10 (s, 3H). TLC-MS (ESI⁻): 554.8 ([M − H]⁻) |

TABLE 2-continued

| Expl. | Reactand | Boronic acid/ Pinacol ester | Product | $^1$H-NMR/MS |
|---|---|---|---|---|
| 4k | 3b | | | $^1$H-NMR (200 MHz, DMSO-d$_6$) δ 12.61 (s, 1H), 9.84 (s, 1H), 9.15 (s, 1H), 8.88 (d, J = 16.2 Hz, 2H), 8.15-7.80 (m, 6H), 7.77-7.60 (m, 2H), 7.51-7.27 (m, 3H), 3.27-3.10 (m, 2H), 1.26 (t, J = 7.2 Hz, 3H). TLC-MS (ESI$^-$): 569.1 ([M − H]$^-$) |
| 4l | 3c | | | $^1$H NMR (200 MHz, DMSO-d$_6$) δ 12.59 (s, 1H), 9.84 (s, 1H), 9.09 (d, J = 18.6 Hz, 2H), 8.86 (d, J = 11.7 Hz, 2H), 8.60 (s, 1H), 8.22 (d, J = 7.3 Hz, 1H), 8.04 (d, J = 7.8 Hz, 1H), 7.78-7.46 (m, 3H), 7.35 (t, J = 8.9 Hz, 1H), 3.24-2.95 (m, 2H), 1.87-1.54 (m, 2H), 0.92 (t, J = 7.4 Hz, 3H). TLC-MS (ESI$^-$): 505.1 ([M − H]$^-$) |
| 4m | 3c | | | $^1$H NMR (200 MHz, DMSO-d$_6$) δ 12.46 (s, 1H), 9.84 (s, 1H), 8.99 (s, 1H), 8.80 (d, J = 7.9 Hz, 2H), 8.02 (d, J = 8.3 Hz, 1H), 7.86-7.58 (m, 4H), 7.34 (t, J = 8.5 Hz, 1H), 7.08 (d, J = 8.3 Hz, 2H), 4.99 (d, J = 5.6 Hz, 1H), 4.70 (t, J = 4.4 Hz, 1H), 4.14-4.02 (m, 1H), 4.00-3.77 (m, 2H), 3.55-3.44 (m, 2H), 3.16 (t, J = 7.7 Hz, 2H), 1.90-1.59 (m, 2H), 0.92 (t, J = 7.4 Hz, 3H). TLC-MS (ESI$^-$): |
| 4n | 3c | | | $^1$H NMR (400 MHz, DMSO-d$_6$) δ 12.61 (s, 1H), 9.15 (d, J = 1.9 Hz, 1H), 8.90 (d, J = 1.2 Hz, 1H), 8.84 (s, 1H), 8.14-8.00 (m, 3H), 7.94 (d, J = 7.9 Hz, 2H), 7.73-7.61 (m, 2H), 7.32 (t, J = 8.6 Hz, 1H), 3.17-3.11 (m, 2H), 1.79-1.67 (m, 2H), 0.92 (t, J = 7.4 Hz, 3H). TLC-MS (ESI$^-$): 547.7 ([M − H]$^-$) |

Example 5: Synthesis of N-[2,4-difluoro-3-[3-(4,4,5,5-tetramethyl-1,3,2-dioxaborolan-2-yl)-9H-pyrido[2,3-b]indole-6-carbonyl]phenyl]propane-1-sulfonamide

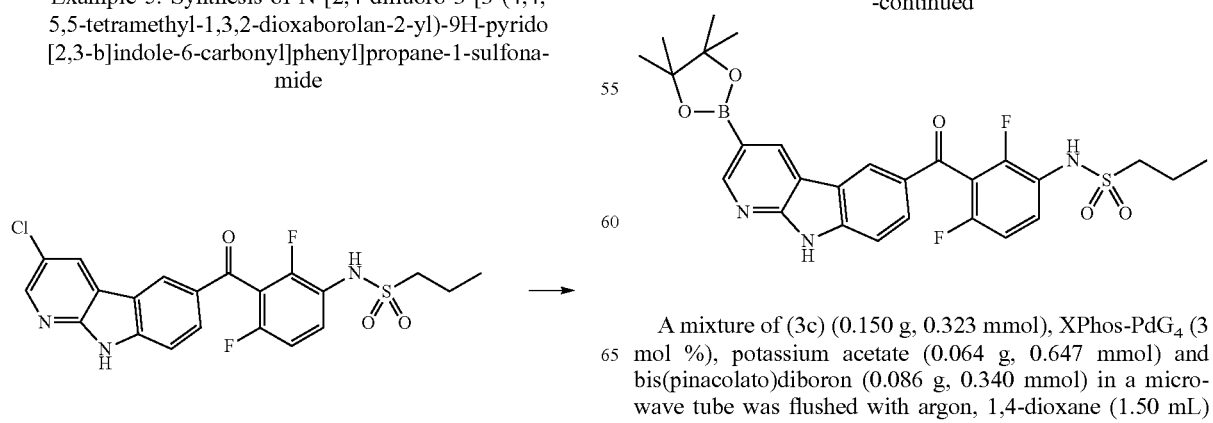

A mixture of (3c) (0.150 g, 0.323 mmol), XPhos-PdG$_4$ (3 mol %), potassium acetate (0.064 g, 0.647 mmol) and bis(pinacolato)diboron (0.086 g, 0.340 mmol) in a microwave tube was flushed with argon, 1,4-dioxane (1.50 mL)

(degassed/argon flushed) was added and the mixture was heated in a microwave (150 W, 110° C.) for 45 min. The reaction was diluted with ethyl acetate (10.0 mL) and washed two times with brine (5.0 mL). The organic layer was dried over sodium sulfate, filtered and the solvent was removed under vacuum. The residue was purified via flash chromatography (silica, gradient: 100% dichloromethane→dichloromethane/ethyl acetate 3/7 v/v). The product was obtained as a white solid (0.137 g, 51%). $^1$H-NMR (200 MHz, DMSO-d$_6$) δ 12.56 (s, 1H), 9.82 (s, 1H), 8.98 (d, J=1.6 Hz, 1H), 8.88 (s, 1H), 8.70 (d, J=1.6 Hz, 1H), 8.09 (dd, J=8.6, 1.6 Hz, 1H), 7.76-7.57 (m, 2H), 7.33 (td, J=9.1, 1.6 Hz, 1H), 3.16 (dd, J=8.8, 6.4 Hz, 2H), 1.87-1.60 (m, 2H), 1.33 (s, 12H), 0.93 (t, J=7.4 Hz, 3H). TLC-MS (ESI$^-$): Calculated 555.18 for $C_{27}H_{28}BF_2N_3O_5S$. Measured 553.8 for [M−H]$^-$. HPLC: $t_R$=9.13 min., purity: 72.9% (254.4 nm), 60.4% (230.4 nm).

Example 6: Synthesis of N-[3-[3-(4-chlorophenyl)-9H-pyrido[2,3-b]indole-6-carbonyl]-2,4-difluorophenyl]propane-1-sulfonamide

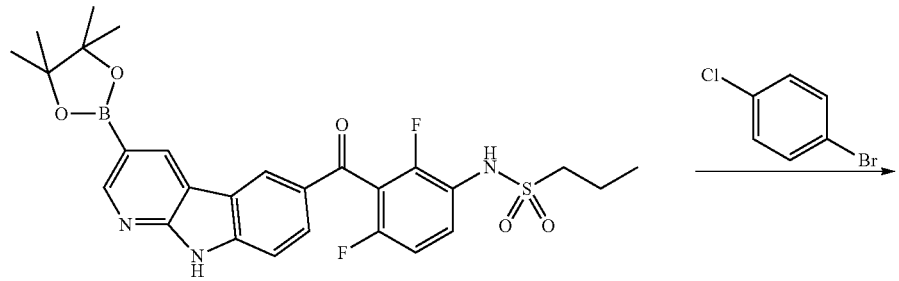

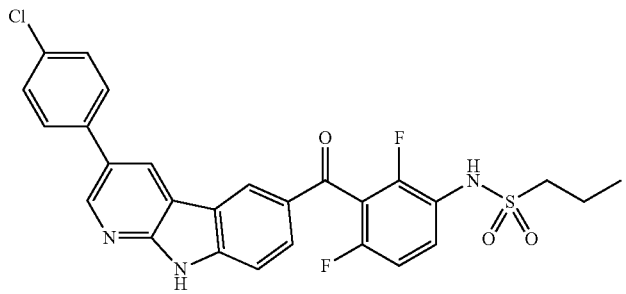

A mixture of N-[2,4-difluoro-3-[3-(4,4,5,5-tetramethyl-1,3,2-dioxaborolan-2-yl)-9H-pyrido[2,3-b] indole-6-carbonyl]phenyl]propane-1-sulfonamide (0.090 mmol), Pd(PPh$_3$)$_4$ (0.004 g, 0.003 mmol) and 1-bromo-4-chlorobenzene (0.0172 g, 0.090 mmol) was flushed with argon in a microwave tube for 12 min. A mixture of 1,4-dioxane and 1.5 aqueous potassium carbonate solution 4/1 v/v (1.0 mL, argon flushed) was added and the reaction was heated in a microwave (50 W, 110° C.) for 45 min. The reaction was quenched with ethyl acetate (15.0 mL) and saturated aqueous ammonia chloride solution (5.0 mL). The organic layer was separated, and the water layer was extracted with ethyl acetate. The combined organic layers were dried over sodium sulfate, filtered and the solvent was removed under vacuum. The residue was purified via flash chromatography (silica, gradient: 100% dichloromethane→dichloromethane/ethyl acetate 3/7 v/v). The product was washed with cold diethyl ether (5.0 mL) and n-pentane (10.0 mL), dried under vacuum to obtain the product as an off-white solid (26 mg, 53%). $^1$H-NMR (400 MHz, DMSO-d$_6$) δ 12.55 (s, 1H), 9.83 (s, 1H), 9.08 (d, J=2.1 Hz, 1H), 8.90-8.74 (m, 2H), 8.03 (dd, J=8.6, 1.3 Hz, 1H), 7.85 (d, J=8.5 Hz, 2H), 7.71-7.63 (m, 2H), 7.57 (d, J=8.5 Hz, 2H), 7.35 (t, J=8.6 Hz, 1H), 3.16 (dd, J=8.7, 6.7 Hz, 2H), 1.79-1.67 (m, 2H), 0.92 (t, J=7.4 Hz, 3H). $^{13}$C-NMR (101 MHz, DMSO-d$_6$) δ 186.8, 156.0 (dd, J=247.6, 8.3 Hz), 152.3, 152.2 (dd, J=251.0, 7.3 Hz), 145.7, 143.5, 136.9, 132.1, 129.1 (dd, J=11.7, 2.7 Hz), 128.9, 128.5, 128.3, 127.9, 127.7, 127.4, 125.0, 122.0 (dd, J=13.5, 3.6 Hz), 120.7, 117.8-117.0 (m), 115.6, 112.4 (dd, J=22.3, 3.2 Hz), 112.0, 53.5, 16.7, 12.5. TLC-MS (ESI$^-$): Calculated 539.09 for $C_{27}H_{20}ClF_2N_3O_3S$. Measured 537.9 for [M−H]$^-$. HPLC: $t_R$=9.49 min, purity: 98.7% (254.4 nm), 98.5% (230.4 nm).

Example 7: Synthesis of N-(3-(3-(6-aminopyridin-3-yl)-9H-pyrido[2,3-b]indole-6-carbonyl)-2,4-difluorophenyl)propane-1-sulfonamide

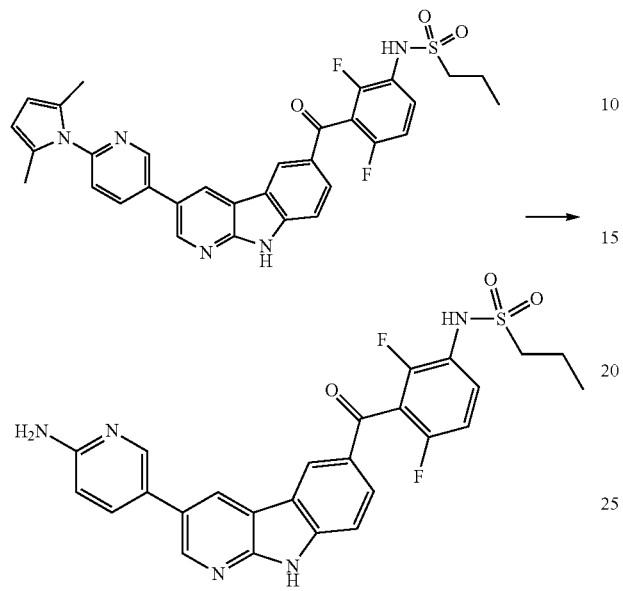

N-[3-[3-[6-(2,5-dimethylpyrrol-1-yl)pyridin-3-yl]-9H-pyrido[2,3-b]indole-6-carbonyl]-2,4-difluorophenyl]propane-1-sulfonamide (0.127 g, 0.212 mmol) was dissolved in a mixture of ethanol (4.40 mL), water (1.10 mL) and triethylamine (0.059 mL, 0.424 mmol) and hydroxylammonium chloride (0.147 g, 2.12 mmol) was added while stirring. The now clear solution was heated at 125° C. for 2 days. The solution was cooled down and poured into an ice-cold mixture of ethyl acetate (10.0 mL) and water (5.0 mL). The organic layer was separated, and the water layer was extracted with ethyl acetate. The combined organic layers were dried over sodium sulfate, filtrated and the solvent was removed under vacuum. The residue was purified via flash chromatography (silica, gradient: 100% DCM→DCM/MeOH 9/1 v/v) to obtain the product as an off-white solid (0.061 g, 54%). $^1$H-NMR (200 MHz, DMSO-$d_6$) δ 12.44 (s, 1H), 9.85 (s, 1H), 9.07-8.49 (m, 3H), 8.37 (s, 1H), 8.11-7.54 (m, 4H), 7.34 (t, J=8.2 Hz, 1H), 6.58 (d, J=8.2 Hz, 1H), 6.10 (s, 2H), 3.24-3.04 (m, 2H), 1.97-1.49 (m, 2H), 1.04-0.81 (m, 3H). TLC-MS (ESI$^-$): Calculated 521.13 for $C_{26}H_{21}F_2N_5O_3S$. Measured 520.0 for [M–H]$^-$.

Example 8: Synthesis of N-(3-(3-chloro-9H-pyrido[2,3-b]indole-6-carbonyl)-2-fluorophenyl)propane-1-sulfonamide Step-1

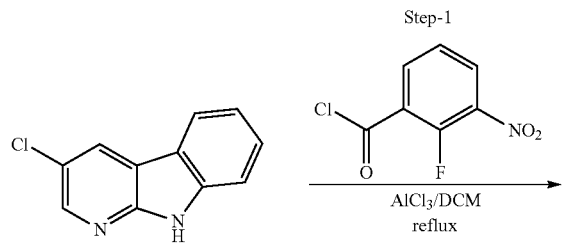

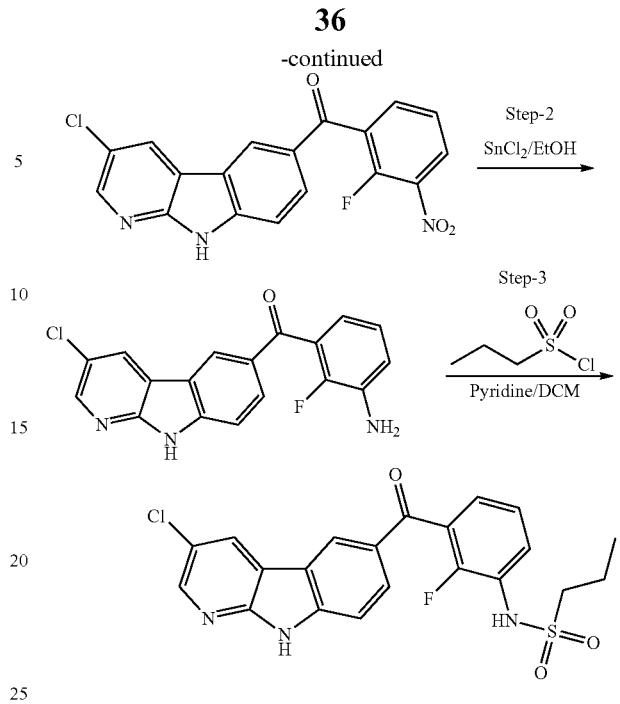

Step 1: (3-chloro-9H-pyrido[2,3-b]indol-6-yl)(2-fluoro-3-nitrophenyl)methanone To anhydrous dichloromethane (20 mL) was added AlCl$_3$ (5 eq., 1.6 g, 12.3 mmol) at room temperature under inert atmosphere. The mixture was stirred at room temperature for 40-50 min., then 3-chloro-9H-pyrido [2,3-b] indole (1 eq, 500 mg, 2.47 mmol) was added. The reaction mixture was further stirred at room temperature for 1 h then cooled to 0° C. Freshly prepared 3,2-fluoro-3-nitro-benzoyl chloride (2 eq, 1 g, 4.94 mmol) was dissolved in 10 mL dichloromethane and drop-wise added to the reaction mixture. The reaction mixture was refluxed until completion of the reaction (monitored by TLC, 24 h). The resulting mixture was then cautiously quenched at 0° C. with Acetonitrile:H$_2$O (1/1 v/v, 10 mL). The precipitated solid was filtered, dried and used in next step without further purification.

Step 2: (3-amino-2-fluorophenyl)(3-chloro-9H-pyrido[2,3-b]indol-6-yl)methanone To crude (3-chloro-9H-pyrido[2,3-b]indol-6-yl)(2-fluoro-3-nitrophenyl)methanone from step 1 in 20 mL of THF was added stannous chloride (4 eq., 820 mg, 4.3 mmol) at room temperature. The suspension was stirred in an oil bath at 65° C. for 24 h. The reaction mixture was then poured into a 20% aq. K$_2$CO$_3$ solution (50 mL). The resulting suspension was stirred for 10-15 min and filtered through a bed of Celite®, the Celite® bed was washed with ethyl acetate. The mixture was extracted with EtOAc (100 mL). The resulting organic layer was washed with a sat. aq NaHCO$_3$ solution and brine, dried over Na$_2$SO$_4$, filtered, and the solvents were removed under reduced pressure. Trituration of the crude residue with MeOH followed by filtration afforded (3-amino-2-fluorophenyl)(3-chloro-9H-pyrido[2,3-b]indol-6-yl)methanone (100 mg).
$^1$H NMR (400 MHz, DMSO-$d_6$) δ=12.50 (bs, 1H), 8.90 (d, J=2.4 Hz, 1H), 8.72 (s, 1H), 8.49 (d, J=2.4 Hz, 1H), 7.94-7.92 (m, 1H), 7.64-7.61 (m, 1H), 7.05-6.95 (m, 2H), 6.64-6.60 (m, 2H), 5.39 (s, 2H). [M+H]+=339.95

Step 3: N-(3-(3-chloro-9H-pyrido[2,3-b]indole-6-carbonyl)-2-fluorophenyl)propane-1-sulfonamide To a stirred solution of (3-amino-2-fluorophenyl)(3-chloro-9H-pyrido[2,3-b]indol-6-yl)methanone (1 eq, 100 mg, 0.29 mmol) in pyridine (1 mL) was added cat. DMAP followed by propane-1-sulfonyl chloride (3 eq, 125 mg (0.1 mL), 0.88 mmol) at room temperature. The reaction mixture was stirred at room temperature for 24 h. After completion of the reaction (TLC), pyridine was removed under reduced pressure, water (15 mL) was added and the mixture was extracted with dichloromethane (50 mL). The resulting organic layer was washed with a 1N HCl solution and brine, dried over $Na_2SO_4$, filtered, and solvents were removed under reduced pressure. The crude compound was purified by preparative reverse phase HPLC to afford N-(3-(3-chloro-9H-pyrido[2,3-b]indole-6-carbonyl)-2-fluorophenyl)propane-1-sulfonamide (15 mg).

$^1$H NMR (400 MHz, DMSO-$d_6$) δ 12.53 (s, 1H), 9.98 (s, 1H), 8.89 (d, J=2.2 Hz, 1H), 8.73 (s, 1H), 8.49 (d, J=2.2 Hz, 1H), 7.98 (d, J=8.6 Hz, 1H), 7.70-7.60 (m, J=8.7 Hz, 2H), 7.40-7.30 (m, J=5.3 Hz, 2H), 3.14 (t, 2H), 1.74 (dd, J=15.1, 7.5 Hz, 2H), 0.95 (t, J=7.4 Hz, 3H), [M+H]+=446

Example 9: Synthesis of N-(3-(3-chloro-9H-pyrido[2,3-b]indole-6-carbonyl)-2,6-difluorophenyl)methanesulfonamide

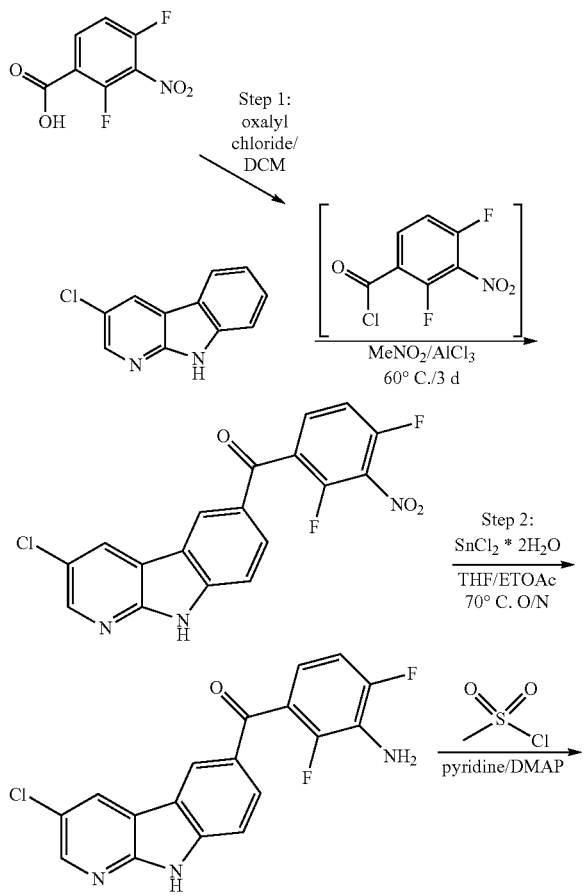

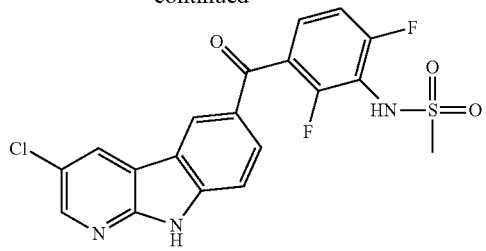

Step 1: (3-chloro-9H-pyrido[2,3-b]indol-6-yl)(2,4-difluoro-3-nitrophenyl)methanone 2,4-Difluoro-3-nitrobenzoic acid (1.3 g, 6.2 mmol, 1.3 eq.) was suspended in DCM (5 mL), oxalyl chloride (846 mg, 6.7 mmol, 1.35 eq.) and some drops of DMF were added. The crude was stirred at rt until complete activation of the carboxylic acid. The volatiles were removed in vacuo and the residue was resolved in $MeNO_2$ (25 mL). In a second flask 3-chloro-9H-pyrido[2,3-b]indole (1.0 g, 4.9 mmol, 1.0 eq.) and $AlCl_3$ (3.3 g, 24.7 mmol, 5.0 eq.) were dissolved in $MeNO_2$ (25 mL) and stirred for at least 30 min. The solution of the activated carboxylic acid was added slowly to the second solution and resulting mixture was stirred for 3 d at 60° C. After TLC-monitoring revealed completion of the reaction, the crude was cooled to 0° C. and MeOH (30 mL) was added very slowly. Water (30 mL) was added and the product was extracted with EtOAc (3×100 mL). The combined organics were dried over sodium sulfate and the solvent was removed under reduced pressure. The residue was suspended in MeOH (20 mL), cooled to −18° C., the precipitate was collected and dried to obtain the pure product (1.2 g, 3.0 mmol, 61%).

ESI-MS ([M−H]$^-$): 386.3 m/z
$^1$H NMR (400 MHz, DMSO-$d_6$): δ 12.56 (s, 1H), 8.79 (d, J=2.3 Hz, 1H), 8.73 (s, 1H), 8.47 (d, J=2.4 Hz, 1H), 8.07-7.99 (m, 2H), 7.72-7.63 (m, 2H).

Step 2: (3-amino-2,4-difluorophenyl)(3-chloro-9H-pyrido[2,3-b]indol-6-yl)methanone (3-chloro-9H-pyrido[2,3-b]indol-6-yl)(2,4-difluoro-3-nitrophenyl)methanone (1.5 g, 3.9 mmol, 1.0 eq.) was suspended in THF (39 mL) and EtOAc (39 mL) and heated to 70° C. $SnCl_2$ dihydrate (4.4 g, 19.3 mmol, 5.0 eq.) was added portion wise and the solution was stirred at 70° C. over night. After HPLC revealed completion of the reaction, a half saturated $NaHCO_3$ solution was added (30 mL) and the resulting solids were removed by filtration. The filtrate was washed with brine and the organics were dried over sodium sulfate. After removal of the solvent the residue was suspended in MeOH (25 mL), cooled to −18° C. and the solids were collected and dried to obtain the product in sufficient purity (1.2 g, 3.4 mmol, 89%).

ESI-MS ([M−H]$^-$): 356.3 m/z
$^1$H NMR (400 MHz, DMSO-$d_6$): δ 12.48 (s, 1H), 8.85 (s, 1H), 8.69 (s, 1H), 8.45 (s, 1H), 7.95 (d, J=8.4 Hz, 1H), 7.62 (d, J=8.5 Hz, 1H), 7.07 (t, J=9.3 Hz, 1H), 6.71 (dd, J=13.7, 7.0 Hz, 1H), 5.47 (s, 2H).

Step 3: N-(3-(3-chloro-9H-pyrido[2,3-b]indole-6-carbonyl)-2,6-difluorophenyl)methane Sulfonamide (3-amino-2,4-difluorophenyl)(3-chloro-9H-pyrido[2,3-b]indol-6-yl)methanone (120 mg, 335 μmol, 1.0 eq.) was dissolved in pyridine (335 μL) and mesyl chloride (58 mg, 503 μmol, 1.5 eq.) was added. 4-DMAP was given to accelerate the reaction. The mixture was stirred at 60° C. over night and diluted with EtOAc (50 mL). This solution was washed with 1 M aqueous HCl solution twice and the organic phase was dried over sodium sulfate. The product was purified applying flash chromatography (DCM/MeOH, 100/0 to 95/5, v/v) obtain the pure product (82 mg, 188 μmol, 56%).

ESI-MS ([M−H]$^-$): 434.2 m/z $^1$H NMR (400 MHz, DMSO-d$_6$): δ 12.54 (s, 1H), 9.75 (s, 1H), 8.84 (d, J=2.4 Hz, 1H), 8.73 (s, 1H), 8.49 (d, J=2.4 Hz, 1H), 7.98 (dd, J=8.6, 1.8 Hz, 1H), 7.67-7.60 (m, 2H), 7.44-7.37 (m, 1H), 3.12 (s, 3H).

Example 10: Synthesis of N-(2,6-difluoro-3-(3-(pyridin-4-yl)-9H-pyrido[2,3-b]indole-6-carbonyl)phenyl)propane-1-sulfonamide

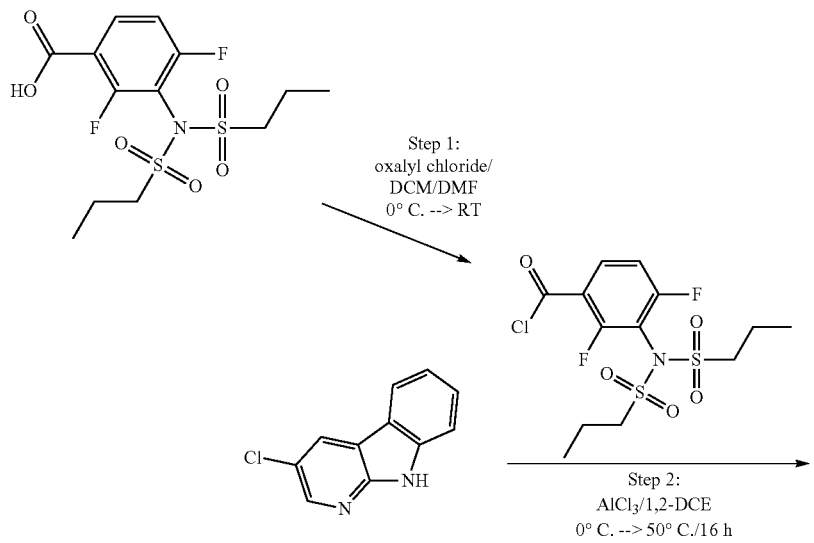
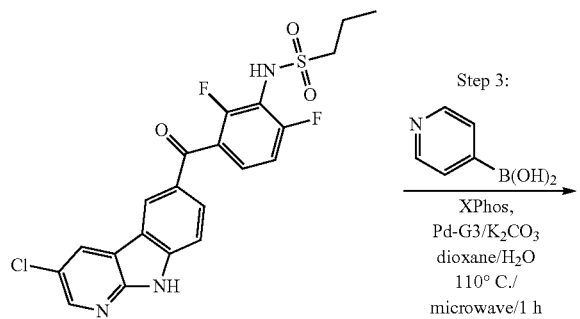
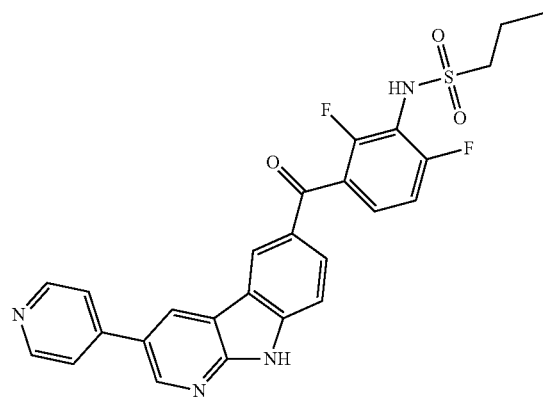

Step 1: 2,4-difluoro-3-(n-propylsulfonamido)benzoic acid was suspended in dry DCM, followed by addition of 1.05 eq. oxalyl chloride and a few drops of DMF. The acid chloride was used for Step 2 without further processing.

Step 2: prepared in analogy to Example 3.
Step 3: prepared in analogy to Example 4a.
Analytical data:
$^1$H NMR (400 MHz, DMSO-d$_6$) δ 12.60 (s, 1H), 9.71 (s, 1H), 9.21 (d, J=2.1 Hz, 1H), 8.99 (d, J=2.2 Hz, 1H), 8.78 (s, 1H), 8.67 (d, J=5.7 Hz, 2H), 8.00 (d, J=8.6 Hz, 1H), 7.89 (d, J=6.0 Hz, 2H), 7.67 (d, J=8.6 Hz, 2H), 7.42 (t, J=8.9 Hz, 1H), 3.18 (dd, J=14.3, 6.7 Hz, 2H), 1.84-1.72 (m, J=15.2, 7.5 Hz, 2H), 0.94 (t, J=7.4 Hz, 3H).
LC-MS (ESI$^+$): 507.10 ([M+H]$^+$)

Example 11: Biological Activity

The kinase activities of the compounds of the invention were measured using KINOMEscan™ Profiling Service at DiscoveRx Corporation, 42501 Albrae St. Fremont, Calif. 94538, USA which is based on a competition binding assay that quantitatively measures the ability of a compound to compete with an immobilized, active-site directed ligand. The assay was performed by combining three components: DNA-tagged kinase; immobilized ligand; and a test compound. The ability of the test compound to compete with the immobilized ligand was measured via quantitative PCR of the DNA tag. The technology is described in detail in Fabian, M. A. et al., A small molecule-kinase interaction map for clinical kinase inhibitors. Nat. Biotechnol., 23, 329-336 (2005) and in Karaman, M. W. et al. A quantitative analysis of kinase inhibitor selectivity, Nat. Biotechnol., 26, 127-132 (2008).

For investigation of the affinity to MKK4, MKK7 and JNK1, the kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SEABLOCK™ (Pierce), 1% BSA, 0.05% TWEEN®20, 1 mM DTT) to remove unbound ligand and to reduce nonspecific binding. Binding reactions were assembled by combining kinases, liganded affinity beads, and test compounds in 1× binding buffer (20% SEA-BLOCK™, 0.17×PBS, 0.05% TWEEN®20, 6 mM DTT). All reactions were performed in polystyrene 96-well plates in a final volume of 0.135 mL. The assay plates were incubated at room temperature with shaking for 1 hour and the affinity beads were washed with wash buffer (lx PBS, 0.05% TWEEN®20). The beads were then re-suspended in elution buffer (lx PBS, 0.05% TWEEN®20, 0.5 11M non-biotinylated affinity ligand) and incubated at room temperature with shaking for 30 minutes. The kinase concentration in the eluates was measured by qPCR.

Average Z' values and standard deviations were calculated for each kinase based on fourteen control wells per experiment in over 135 independent experiments spanning a period of sixteen months. Average Z'=0.71.

Potency of Test Compounds:
The compounds were screened at the indicated concentrations and results for binding interactions are reported as [% of control], where lower numbers indicate stronger binding, i.e. higher potency.

Details regarding the kinases tested are given in table 3 below.

The test compounds were provided as 10 mM stock solutions. The test solutions at indicated final concentrations were prepared at DiscoverX. The results are given in table 4 below.

TABLE 3

|  | MKK4 | MKK7 | JNK1 |
| --- | --- | --- | --- |
| Group | STE | STE | CMCG |
| Kinase Construct | Partial Length | Full Length | Full length |
| Accession Number | NP_003001.1 | NP_660186.1 | NP_002741.1 |
| Species | Human | Human | Human |
| Kinase Form | Wild Type | Wild Type | Wild Type |
| Expression System | Mammalian | Mammalian | Mammalian |
| Amino Acid Start/Stop | S84/D399 | M1/R419 | M1/Q384 |
| Average Z' Panel | 0.67 | 0.78 | 0.79 |

MKK4 Potency:
Potency of Examples 3a-3c, 4a-4n and 6-8 against the protein kinase MKK4, expressed as residual percent of control binding (PoC), was determined at a concentration of 100 nM. The results are given in table 4 below.

TABLE 4

| Example | MKK4 |
| --- | --- |
| 3c | + + |
| 4a | + + + |
| 4b | + + |
| 4c | + + |
| 4d | + + |
| 4e | + + + |
| 4f | + + |
| 4h | + + + |
| 4i | + + + |
| 4j | + + + |
| 4k | + + + |
| 4l | + + + |
| 4m | + + + |
| 4n | + + + |
| 6 | + |
| 7 | + + + |
| 8 | + |
| 9 | + + + |

PoC < 1 = "+++"; 1 ≤ PoC < 10 = "++"; 10 ≤ PoC < 30 = "+"; PoC ≥ 30 = "O".

Selectivity Against JNK1:
Selectivity of Examples 3a-3c, 4a-4n and 6-8 against the off-target JNK1, determined by calculation of the ratio of residual percent of control binding (PoC) to JNK1 and MKK4, was determined at a concentration of 100 nM. The results are given in table 5 below.

TABLE 5

| Example | Selectivity vs. JNK1 |
| --- | --- |
| 3c | +++ |
| 4a | +++ |
| 4b | +++ |
| 4c | +++ |
| 4d | +++ |
| 4e | +++ |
| 4f | +++ |
| 4h | +++ |
| 4i | +++ |
| 4j | +++ |

TABLE 5-continued

| Example | Selectivity vs. JNK1 |
|---|---|
| 4k | +++ |
| 4l | +++ |
| 4m | +++ |
| 4n | +++ |
| 6 | + |
| 7 | +++ |
| 8 | +++ |
| 9 | +++ |

PoC(JNK1)/PoC(MKK4) ≥ 30 = "+++"; 30 > PoC(JNK1)/PoC(MKK4) ≥ 10 = "++"; 10 > PoC(JNK1)/PoC(MKK4) ≥ 3 = "+"; PoC(JNK1)/PoC(MKK4) < 3 = "O".

MKK4 Potency and Selectivity Against MKK7:

Selectivity of Examples 3a-3c, 4a-4n and 6-8 against the off-target MKK7, determined by calculation of the ratio of residual percent of control binding (PoC) to MKK7 and MKK4, was determined at a concentration of 100 nM. The results are given in table 6 below.

TABLE 6

| Example | Selectivity vs. MKK7 |
|---|---|
| 3c | +++ |
| 4a | +++ |
| 4b | +++ |
| 4c | +++ |
| 4d | +++ |
| 4e | +++ |
| 4f | +++ |
| 4h | +++ |
| 4i | +++ |
| 4j | +++ |
| 4k | +++ |
| 4l | +++ |
| 4m | +++ |
| 4n | +++ |
| 6 | + |
| 7 | +++ |
| 8 | +++ |
| 9 | +++ |

PoC(MKK7)/PoC(MKK4) ≥ 30 = "+++"; 30 > PoC(MKK7)/PoC(MKK4) ≥ 10 = "++"; 10 > PoC(MKK7)/PoC(MKK4) ≥ 3 = "+"; PoC(MKK7)/PoC(MKK4) < 3 = "O".

MKK4 Potency and Selectivity Against BRaf:

Selectivity of Examples 3a-3c, 4a-4n and 6-8 against the off-target BRaf, determined by calculation of the ratio of residual percent of control binding (PoC) to BRaf and MKK4, was determined at a concentration of 100 nM. The results are given in table 7 below.

TABLE 7

| Example | Selectivity vs. BRaf |
|---|---|
| 3c | +++ |
| 4a | +++ |
| 4b | +++ |
| 4c | +++ |
| 4d | +++ |
| 4e | +++ |
| 4f | +++ |
| 4h | +++ |
| 4i | +++ |
| 4j | +++ |
| 4k | +++ |
| 4l | +++ |
| 4m | +++ |
| 4n | +++ |
| 6 | + |
| 7 | +++ |
| 8 | +++ |
| 9 | +++ |

PoC(BRaf)/PoC(MKK4) ≥ 30 = "+++"; 30 > PoC(BRaf)/PoC(MKK4) ≥ 10 = "++"; 10 > PoC(BRaf)/PoC(MKK4) ≥ 3 = "+".

The invention claimed is:

1. A compound having formula (Ia) or a pharmaceutically acceptable salt, solvate or optical isomer thereof,

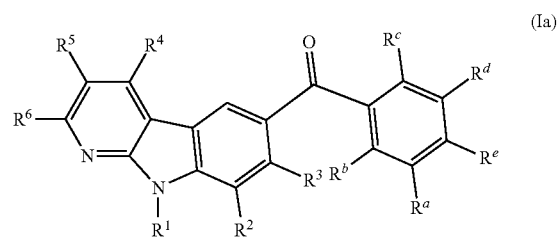

(Ia)

wherein the variables in formula (Ia) have the meanings as follows:
$R^1$ is H or alkyl;
$R^2$ is H or alkyl;
$R^3$ is H or alkyl;
$R^a$ is —$NR^{10}SO_2R^{12}$;
$R^b$, $R^c$, $R^d$ and $R^e$ are independently selected from
  H, and
  halogen,
  wherein 1, 2 or 3 of $R^b$, $R^c$, $R^d$ and $R^e$ are halogen, and the other ones are H;
$R^4$ is H or alkyl;
$R^5$ is selected from
  a) halogen,
  b) phenyl which is optionally substituted with 1 or 2 groups independently selected from halogen, hydroxy, $R^{11}O$—, $COOR^{10}$, $R^{10}R^{10}N$—CO—, $R^{10}R^{11}NSO_2$—, and tetrazolyl, and
  c) pyridyl which is optionally substituted with 1 or 2 groups independently selected from —$NR^{10}R^{10}$, $R^{10}R^{11}N$—$SO_2$—, $R^{10}R^{11}N$—CO— and pyrrolyl which is optionally substituted with 1 or 2 alkyl groups;
$R^6$ is H or alkyl;
$R^{10}$ at each occurrence independently is H or alkyl;
$R^{11}$ is H, or alkyl, which is optionally substituted with 1 or 2 hydroxy groups;
$R^{12}$ is alkyl.

2. The compound or a pharmaceutically acceptable salt, solvate or optical isomer thereof, of claim 1 having formula (Ib) or (Ic)

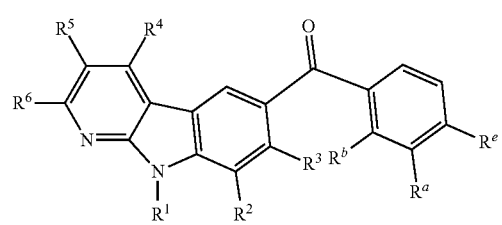

(Ib)

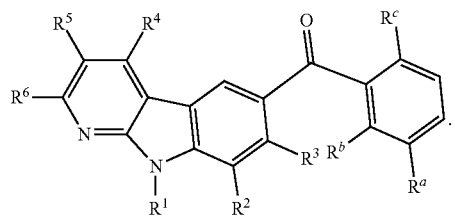

(Ic)

3. The compound or a pharmaceutically acceptable salt, solvate or optical isomer thereof, of claim 1, wherein
   a) $R^b$ and $R^e$ are both halogens, or
   b) $R^b$ and $R^c$ are both halogens.

4. The compound or a pharmaceutically acceptable salt, solvate or optical isomer thereof, of claim 2, wherein in formula (Ib) $R^b$ and $R^e$ are fluorine and in formula (Ic) $R^b$ and $R^c$ are fluorine.

5. The compound or a pharmaceutically acceptable salt, solvate or optical isomer thereof, of claim 1, wherein $R^1$, $R^2$, $R^3$, $R^4$, and $R^6$ are H.

6. The compound or a pharmaceutically acceptable salt, solvate or optical isomer thereof, of claim 1, wherein $R^{10}$ is H or alkyl.

7. The compound or a pharmaceutically acceptable salt, solvate or optical isomer thereof, of claim 1, wherein $R^{11}$ is alkyl.

8. The compound of claim 1, selected from the group consisting of

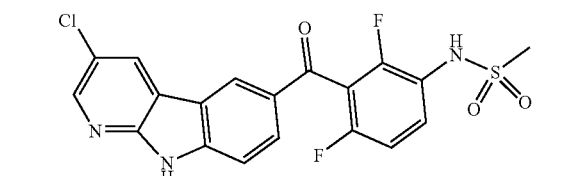

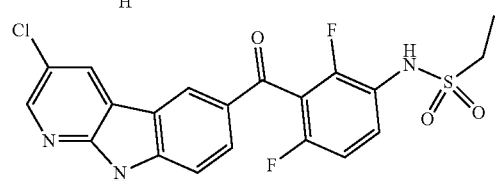

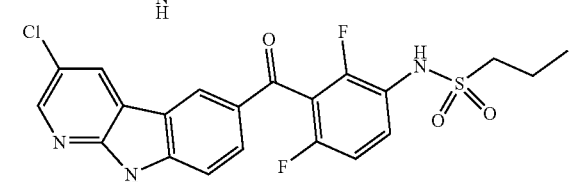

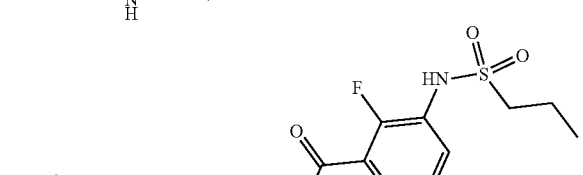

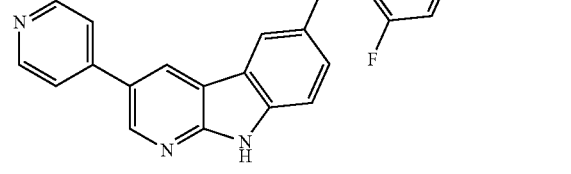

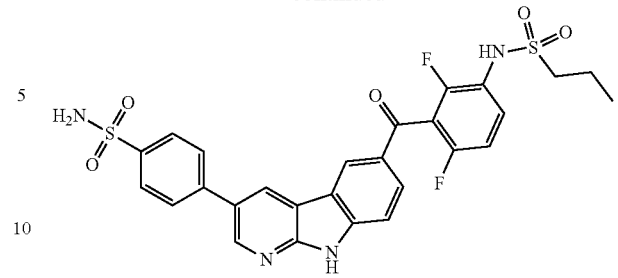

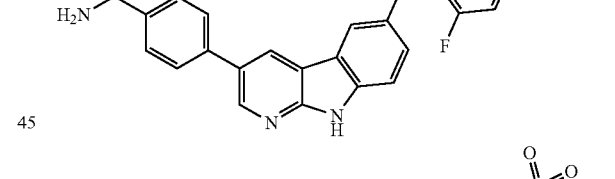

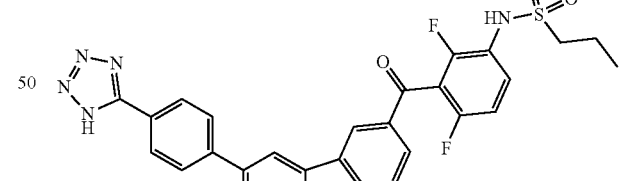

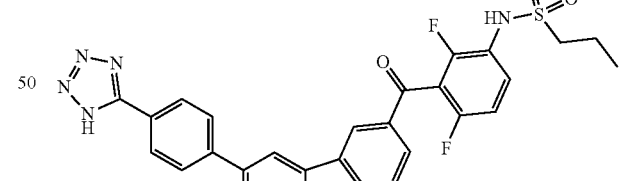

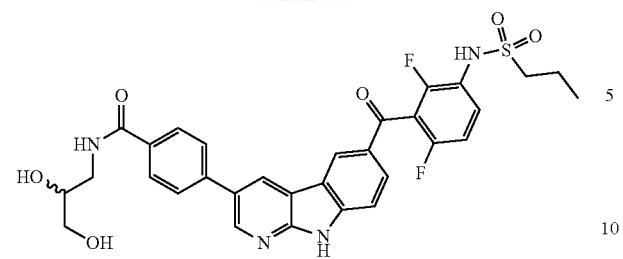
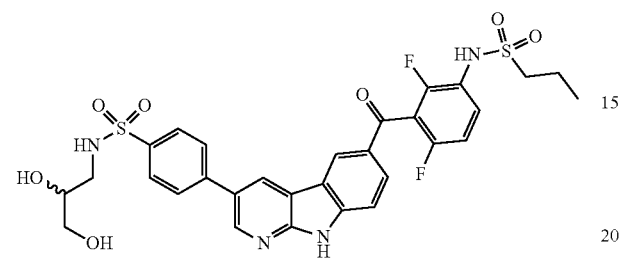
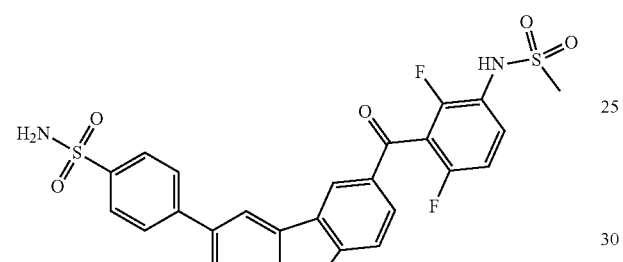
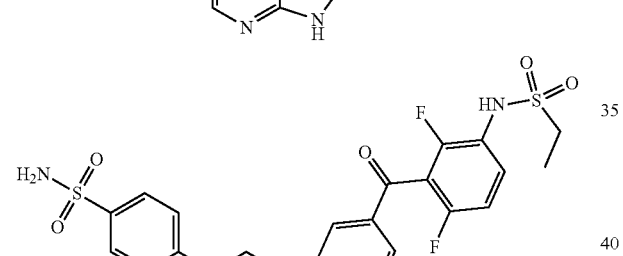
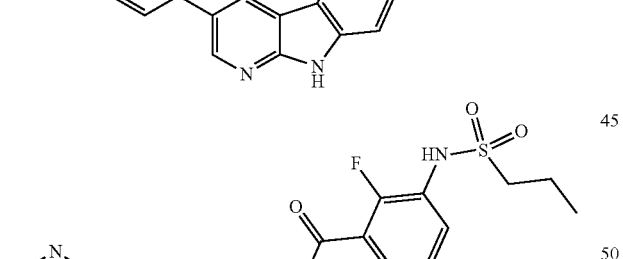
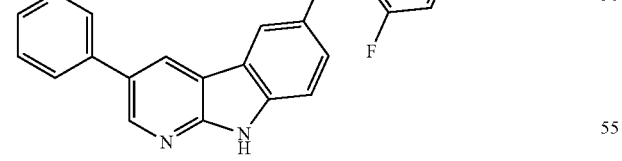
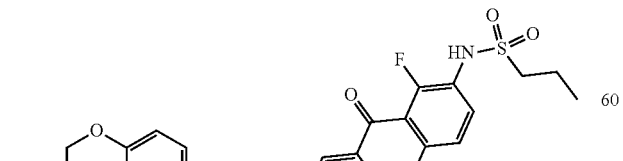
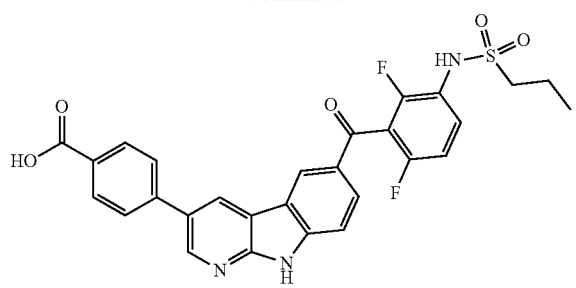
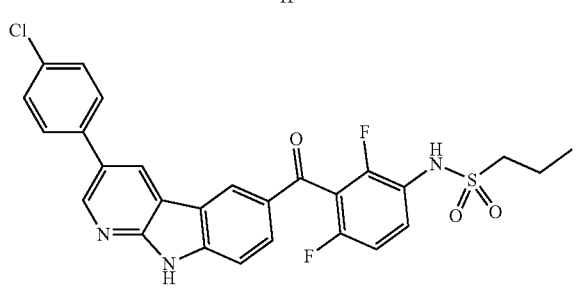
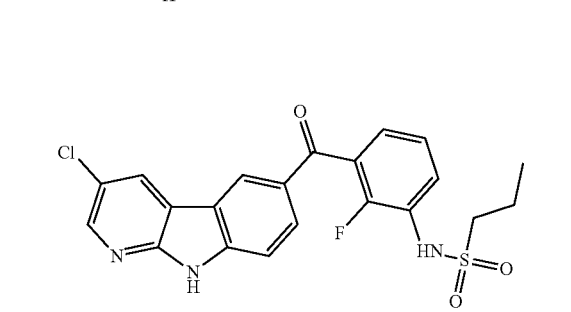
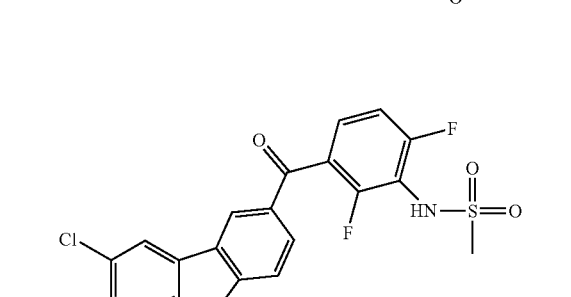
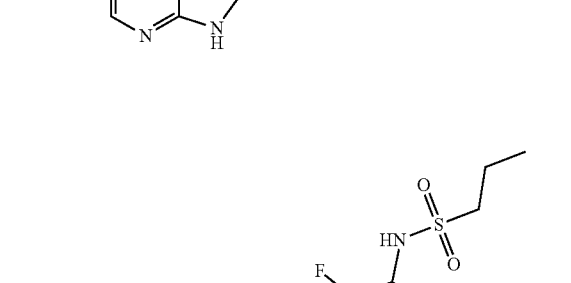
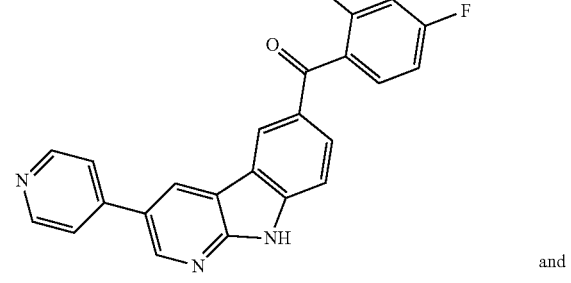
and -continued

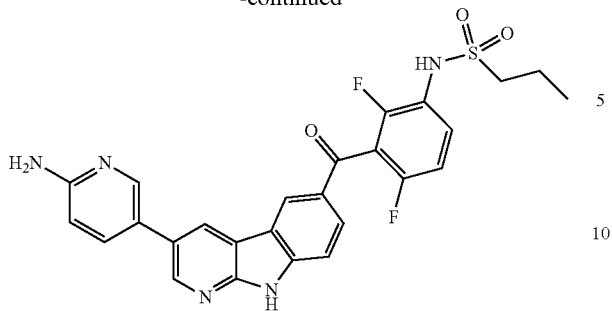

or a pharmaceutically acceptable salt, solvate or optical isomer thereof.

9. A pharmaceutical composition comprising a compound or a pharmaceutically acceptable salt, solvate or optical isomer thereof as defined in claim 1.

10. A method for selectively inhibiting protein kinase MKK4 over protein kinases JNK1 and MKK7 in a subject, comprising administering an effective amount of a compound of formula (Ia) or a pharmaceutically acceptable salt, solvate or optical isomer thereof as defined in claim 1 to the subject.

11. A method for promoting liver regeneration or reducing hepatocyte death in a subject in need thereof, comprising administering an effective amount of a compound of formula (Ia) or a pharmaceutically acceptable salt, solvate or optical isomer thereof as defined in claim 1 to the subject.

* * * * *